US011560437B2

(12) United States Patent
Zhukovsky et al.

(10) Patent No.: US 11,560,437 B2
(45) Date of Patent: *Jan. 24, 2023

(54) STABLE MULTISPECIFIC ANTIBODIES

(71) Applicant: BIOMUNEX PHARMACEUTICALS, Paris (FR)

(72) Inventors: Eugene Zhukovsky, Bethel, CT (US); Olivier Leger, Saint Sixt (FR); Richard J. Morse, Bethel, CT (US)

(73) Assignee: BIOMUNEX PHARMACEUTICALS, Paris (FR)

( * ) Notice: Subject to any disclaimer, the term of this patent is extended or adjusted under 35 U.S.C. 154(b) by 311 days.

This patent is subject to a terminal disclaimer.

(21) Appl. No.: 16/498,421

(22) PCT Filed: Mar. 27, 2018

(86) PCT No.: PCT/EP2018/057819
§ 371 (c)(1),
(2) Date: Sep. 27, 2019

(87) PCT Pub. No.: WO2018/178101
PCT Pub. Date: Oct. 4, 2018

(65) Prior Publication Data
US 2020/0299413 A1   Sep. 24, 2020

(30) Foreign Application Priority Data
Mar. 27, 2017 (EP) .................................. 17305353

(51) Int. Cl.
*C07K 16/46* (2006.01)
*C07K 16/28* (2006.01)
*C12N 15/63* (2006.01)
*A61K 39/00* (2006.01)

(52) U.S. Cl.
CPC ........ *C07K 16/468* (2013.01); *C07K 16/2827* (2013.01); *C12N 15/63* (2013.01); *A61K 2039/505* (2013.01); *C07K 2317/31* (2013.01); *C07K 2317/522* (2013.01); *C07K 2317/55* (2013.01); *C07K 2317/732* (2013.01); *C07K 2317/92* (2013.01)

(58) Field of Classification Search
CPC .......... C07K 2317/522; C07K 2317/31; C07K 16/468
USPC ............................................ 424/133.1, 136.1
See application file for complete search history.

(56) References Cited

U.S. PATENT DOCUMENTS

| 9,631,031 | B2 * | 4/2017 | Kadouche | C07K 16/2896 |
|---|---|---|---|---|
| 9,738,707 | B2 * | 8/2017 | Taylor | C07K 16/00 |
| 10,487,156 | B2 * | 11/2019 | Blanchetot | C07K 1/22 |
| 10,633,456 | B1 | 4/2020 | Boyd-Kirkup et al. | |
| 10,662,241 | B1 | 5/2020 | Boyd-Kirkup et al. | |
| 10,815,310 | B2 * | 10/2020 | Kadouche | C07K 16/2896 |
| 11,046,776 | B2 | 6/2021 | Lazar et al. | |
| 2002/0004587 | A1 | 1/2002 | Miller et al. | |
| 2014/0113348 | A1 | 4/2014 | Williams et al. | |
| 2014/0242076 | A1 * | 8/2014 | Kadouche | C07K 16/2896 435/69.6 |
| 2014/0341906 | A1 * | 11/2014 | Taylor | C07K 16/18 435/69.6 |
| 2016/0297891 | A1 * | 10/2016 | Ng | A61P 35/00 |
| 2017/0342166 | A1 * | 11/2017 | Blanchetot | C07K 16/468 |
| 2018/0022829 | A1 * | 1/2018 | Kadouche | C07K 16/2833 435/69.6 |
| 2018/0057598 | A1 | 3/2018 | Lazar et al. | |
| 2019/0153104 | A1 | 5/2019 | Zhukovsky et al. | |
| 2019/0300610 | A1 | 10/2019 | Boyd-Kirkup et al. | |
| 2019/0300624 | A1 | 10/2019 | Boyd-Kirkup et al. | |
| 2019/0330377 | A1 | 10/2019 | Zhukovsky et al. | |
| 2020/0010559 | A1 * | 1/2020 | Zhukovsky | C07K 16/2827 |
| 2020/0283524 | A1 | 9/2020 | Xu et al. | |
| 2020/0308275 | A1 | 10/2020 | Boyd-Kirkup et al. | |
| 2020/0308308 | A1 | 10/2020 | Boyd-Kirkup et al. | |
| 2021/0024651 | A1 | 1/2021 | Boyd-Kirkup et al. | |
| 2021/0155712 | A1 | 5/2021 | Boyd-Kirkup et al. | |

FOREIGN PATENT DOCUMENTS

| CA | 2 929 256 | 5/2015 |
|---|---|---|
| JP | 2014-522644 | 9/2014 |
| JP | 2016-509014 | 3/2016 |
| WO | WO 2012/088461 | 6/2012 |
| WO | WO 2012/131555 | 10/2012 |
| WO | WO 2013/005194 | 1/2013 |
| WO | WO 2014/028776 | 2/2014 |
| WO | WO 2014/124326 | 8/2014 |
| WO | WO 2015/149077 | 10/2015 |
| WO | WO 2015/173756 | 11/2015 |
| WO | WO 2016/014974 | 1/2016 |
| WO | WO 2016/172485 | 10/2016 |
| WO | WO 2017/162890 | 9/2017 |

(Continued)

OTHER PUBLICATIONS

Debiec et al., (J. Phys. Chem. B 2014, 118, 6561-6569).*
Meuzelaar et al. (Biophysical Journal 110, 2328-2341, (Jun. 7, 2016)).*
Hu et al., (Cancer Res; 75(1):1-14; Jan. 1, 2015; Published Online First Nov. 4, 2014).*
Moore,G.L.et al., "1798 Tuning T Cell Affinity Improves Efficacy and Safety of Anti-CD38xAnti-CD3 Bispecific Antibodiesin Monkeys—a Potential Therapy for Multiple Myeloma" presented Dec. 5, 2015, 57th Annual Meeting & Exposition, Orlando, Florida, pp. 1-3).*

(Continued)

*Primary Examiner* — Lynn A Bristol
(74) *Attorney, Agent, or Firm* — Saliwanchik, Lloyd & Eisenschenk

(57) ABSTRACT

The invention relates to multispecific antibody constructs comprising Fab fragments having a particular set of mutations at the interface of the CH1 and CL domains, the mutations preventing heavy chain/light chain mispairing.

14 Claims, 7 Drawing Sheets

Specification includes a Sequence Listing.

(56) References Cited

FOREIGN PATENT DOCUMENTS

| WO | WO 2017/186950 | 11/2017 |
|----|----------------|---------|
| WO | WO 2018/127608 | 7/2018  |

OTHER PUBLICATIONS

Genmab, "Genmab Announces Studies of Daratumumab in Combination with Atezolizumab in a Solid Tumor and Multiple Myeloma" Company Announcement No. 15, Mar. 21, 2016, retrieved from the Internet on Jun. 1, 2017: URL:https://www.clinicalleader.com/doc/genmab-announces-studies-of-daratumumab-in-combination-with-atezolizumab-0001, pp. 1-2.

Written Opinion in International Application No. PCT/EP2017/057220, dated Jun. 26, 2017, pp. 1-6.

Chu, S. Y. et al. "Immunotherapy with Long-Lived Anti-CD38 x Anti-CD3 Bispecific Antibodies Stimulates Potent T Cell-Mediated Killing of Human Myeloma Cell Lines and CD38+ Cells in Monkeys: A Potential Therapy for Multiple Myeloma" 2014, p. 1.

Lloyd, C. et al., "Modelling the human immune response: performance of a $10^{11}$ human antibody repertoire against a broad panel of therapeutically relevant antigens" Protein Engineering Design & Selection, 2009, vol. 22, pp. 159-168.

Edwards, B. M. et al., "The Remarkable Flexibility of the Human Antibody Repertoire; Isolation of Over One Thousand Different Antibodies to a Single Protein, BLyS" J Mol Biol., 2003, vol. 14, No. 334(1), pp. 103-118.

Goel, M. et al., "Plasticity within the Antigen-Combining Site May Manifest as Molecular Mimicry in the Humoral Immune Response" The Journal of Immunology, 2004, vol. 173, No. 12, pp. 7358-7367.

Malia, T. J. et al., "Epitope mapping and structural basis for the recognition of phosphorylated tau by the anti-tau antibody AT8" Proteins, 2016, vol. 84, pp. 427-434.

Barthelemy, P. A. et al., "Comprehensive Analysis of the Factors Contributing to the Stability and Solubility of Autonomous Human $V_H$ Domains" Journal of Biological Chemistry, 2008, vol. 283, pp. 3639-3654.

Beiboer, S. H. W. et al., "Guided Selection of a Pan Carcinoma Specific Antibody Reveals Similar Binding Characteristics yet Structural Divergence Between the Original Murine Antibody and its Human Equivalent" Journal of Molecular Biology, 2000, vol. 296, pp. 833-849.

Choi, Y. et al., "Predicting antibody complementarity determining region structures without classification" Molecular Biosystems, 2011, vol. 7, pp. 3327-3334.

De Genst, E. et al., "Antibody repertoire development in camelids" Developmental and Comparative Immunology, 2006, vol. 30, pp. 187-198.

Griffiths, A. D. et al., "Human anti-self antibodies with high specificity from phage display libraries" The EMBO Journal, 1993, vol. 12, pp. 725-734.

Klimka, A. et al., "Human anti-CD30 recombinant antibodies by guided phage antibody selection using cell panning" British Journal of Cancer, 2000, vol. 83, pp. 252-260.

Ward, E. S. et al. "Binding activities of a repertoire of single immunoglobulin variable domains secreted from Escherichia coli" Nature, 1989, vol. 341, pp. 544-546.

Holm, P. et al., "Functional mapping and single chain construction of the anti-cytokeratin 8 monoclonal antibody TS1" Mol. Immunol., Feb. 2007, vol. 44 No. 6, pp. 1075-1084.

Rudikoff, S. et al., "Single amino acid substitution altering antigen-binding specificity" Proc. Natl. Acad. Sci. USA., 1982, vol. 79, pp. 1979-1983.

MacCallum, R. M. et al., "Antibody-antigen Interactions: Contact Analysis and Binding Site Topography" J. Mol. Biol., Oct. 11, 1996, vol. 262, No. 5, pp. 732-745.

Written Opinion in International Application No. PCT/EP2018/050481, dated Mar. 26, 2018, pp. 1-10.

Chen, X. et al. "Fusion Protein Linkers: Property, Design and Functionality" Adv Drug Deliv Rev., Oct. 15, 2013, vol. 65, No. 10, pp. 1357-1369.

Reusch, U. et al. "A tetravalent bispecific TandAb (CD19/CD3), AFM 11, efficiently recruits T cells for the potent lysis of CD19+ tumor cells" MAbs, May/Jun. 2015, vol. 7, No. 3, pp. 584-604.

Written Opinion in International Application No. PCT/EP2017/060280, dated Jul. 4, 2017, pp. 1-8.

Assenat, E. et al. "Dual targeting of HER1/EGFR and HER2 with cetuximab and trastuzumab in patients with metastatic pancreatic cancer after gemcitabine failure: results of the "Therapy" phase 1-2 trial" Oncotarget, Feb. 28, 2015, pp. 12796-12808, vol. 6, No. 14.

Wu, X. et al. "Fab-based bispecific antibody formats with robust biophysical properties and biological activity" mAbs, May/Jun. 2015, pp. 470-482, vol. 7, Issue 3.

Worn, A. et al. "Stability Engineering of Antibody Single-chain Fv Fragments" J. Mol. Biol., 2001, vol. 305, pp. 989-1010.

Wang, S. et al. "Effective suppression of breast tumor growth by an anti-EGFR/ErbB2 bispecific antibody" Cancer Letters, 2012, vol. 325, pp. 214-219.

https://clinicaltrials.gov/ct2/show/NCT00551421 pp. 1-12 (Aug. 11, 2021).

Biotechnology, Chemical, Pharmaceutical (BCP) Partnership Meeting (SPE Dan Kolker, Sep. 17, 2020; pp. 1-36).

Brinkmann, U. et al. "The making of bispecific antibodies" MABS, 2017, vol. 9, No. 2, pp. 182-212.

Genmab Press Release, "Genmab Announces Studies of Daratumumab in Combination with Atezolizumab in a Solid Tumor and Multiple Myeloma" Mar. 21, 2016, pp. 1-2, retrieved from Internet: http://files.shareholder.com/downloads/AMDA-KPIBN/0x0x882184/5D77EB62-231D-41DA-9416-39D816CF878C/15_Dara%20atezolizumab%20combo_210316_uk.pdf.

Golay, J. et al. "Design and Validation of a Novel Generic Platform for the Production of Tetravalent IgG1-like Bispecific Antibodies" The Journal of Immunology, 2016, pp. 3199-3211, vol. 196, Supplemental Table, p. 1.

Mazor, Y. et al. "Enhanced tumor-targeting selectivity by modulating bispecific antibody binding affinity and format valence" Scientific Reports, Jan. 9, 2017, pp. 1-11, vol. 7.

Written Opinion in International Application No. PCT/EP2018/057819, dated Jul. 24, 2018, pp. 1-11.

\* cited by examiner

SEQUENCE LISTING

<160> NUMBER OF SEQ ID NOS: 21

<210> SEQ ID NO 1
<211> LENGTH: 34
<212> TYPE: PRT
<213> ORGANISM: Artificial Sequence
<220> FEATURE:
<223> OTHER INFORMATION: Linker sequence 1
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 1

Glu Pro Lys Xaa Cys Asp Lys Xaa His Xaa Xaa Pro Pro Xaa Pro Ala
1               5                   10                  15

Pro Glu Leu Leu Gly Gly Pro Xaa Xaa Pro Pro Xaa Pro Xaa Pro Xaa
            20                  25                  30

Gly Gly

<210> SEQ ID NO 2
<211> LENGTH: 34
<212> TYPE: PRT
<213> ORGANISM: Artificial Sequence
<220> FEATURE:
<223> OTHER INFORMATION: Linker sequence 2

<400> SEQUENCE: 2

Glu Pro Lys Ser Cys Asp Lys Thr His Thr Ser Pro Pro Ala Pro Ala
1               5                   10                  15

Pro Glu Leu Leu Gly Gly Pro Gly Gly Pro Pro Gly Pro Gly Pro Gly
            20                  25                  30

Gly Gly

<210> SEQ ID NO 3
<211> LENGTH: 34
<212> TYPE: PRT
<213> ORGANISM: Artificial Sequence
<220> FEATURE:
<223> OTHER INFORMATION: Linker sequence 3

<400> SEQUENCE: 3

```
Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Ala Pro Ala
            20                  25                  30

Gly Gly

<210> SEQ ID NO 4
<211> LENGTH: 34
<212> TYPE: PRT
<213> ORGANISM: Artificial Sequence
<220> FEATURE:
<223> OTHER INFORMATION: Linker sequence 4

<400> SEQUENCE: 4

Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Gly Pro Ala Pro Gly
            20                  25                  30

Gly Gly

<210> SEQ ID NO 5
<211> LENGTH: 34
<212> TYPE: PRT
<213> ORGANISM: Artificial Sequence
<220> FEATURE:
<223> OTHER INFORMATION: Linker sequence 5

<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro Ser Thr Pro Pro Thr Pro Ser Pro Ser
            20                  25                  30

Gly Gly

<210> SEQ ID NO 6
<211> LENGTH: 34
<212> TYPE: PRT
<213> ORGANISM: Artificial Sequence
<220> FEATURE:
<223> OTHER INFORMATION: Linker sequence 6

<400> SEQUENCE: 6

Glu Pro Lys Ser Cys Asp Lys Thr His Thr Ser Pro Pro Ser Pro Ala
1               5                   10                  15

Pro Glu Leu Leu Gly Gly Pro Ser Thr Pro Pro Thr Pro Ser Pro Ser
            20                  25                  30

Gly Gly

<210> SEQ ID NO 7
<211> LENGTH: 702
<212> TYPE: PRT
<213> ORGANISM: Artificial Sequence
<220> FEATURE:
<223> OTHER INFORMATION: heavy chain

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30
```

-continued

```
Ala Met Ser Trp Val Arg Gln Ala Pro Gly Lys Gly Leu Glu Trp Val
             35                  40                  45
Ser Ala Ile Ser Gly Ser Gly Gly Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Phe Cys
                 85                  90                  95
Ala Lys Asp Lys Ile Leu Trp Phe Gly Glu Pro Val Phe Asp Tyr Trp
             100                 105                 110
Gly Gln Gly Thr Leu Val Thr Val Ser Ser Ala Ser Thr Lys Gly Pro
             115                 120                 125
Ser Val Phe Pro Gln Ala Pro Ser Ser Lys Ser Thr Ser Gly Gly Thr
 130                 135                 140
Ala Ala Leu Gly Cys Leu Val Lys Asp Tyr Phe Pro Glu Pro Val Thr
 145                 150                 155                 160
Val Ser Trp Asn Ser Gly Ala Leu Thr Ser Gly Val His Thr Phe Pro
                 165                 170                 175
Ala Val Leu Gln Ser Ser Gly Leu Tyr Ser Leu Ser Val Val Thr
             180                 185                 190
Val Pro Ser Ser Ser Leu Gly Thr Gln Thr Tyr Ile Cys Asn Val Asn
             195                 200                 205
His Lys Pro Ser Asn Thr Lys Val Asp Lys Arg Val Glu Pro Lys Ser
     210                 215                 220
Cys Asp Lys Thr His Thr Ser Pro Pro Ala Pro Ala Pro Glu Leu Leu
225                 230                 235                 240
Gly Gly Pro Ala Ala Pro Pro Ala Pro Ala Pro Ala Gly Gly Glu Val
                 245                 250                 255
Gln Leu Val Glu Ser Gly Gly Leu Val Gln Pro Gly Gly Ser Leu
             260                 265                 270
Arg Leu Ser Cys Ala Ala Ser Gly Phe Thr Phe Ser Asp Ser Trp Ile
             275                 280                 285
His Trp Val Arg Gln Ala Pro Gly Lys Gly Leu Glu Trp Val Ala Trp
     290                 295                 300
Ile Ser Pro Tyr Gly Gly Ser Thr Tyr Tyr Ala Asp Ser Val Lys Gly
305                 310                 315                 320
Arg Phe Thr Ile Ser Ala Asp Thr Ser Lys Asn Thr Ala Tyr Leu Gln
                 325                 330                 335
Met Asn Ser Leu Arg Ala Glu Asp Thr Ala Val Tyr Tyr Cys Ala Arg
             340                 345                 350
Arg His Trp Pro Gly Gly Phe Asp Tyr Trp Gly Gln Gly Thr Leu Val
             355                 360                 365
Thr Val Ser Ser Ala Ser Thr Lys Gly Pro Ser Val Phe Pro Leu Ala
 370                 375                 380
Pro Ser Ser Lys Ser Thr Ser Gly Gly Thr Ala Ala Leu Gly Cys Leu
385                 390                 395                 400
Val Lys Asp Tyr Phe Pro Glu Pro Val Thr Val Ser Trp Asn Ser Gly
                 405                 410                 415
Ala Leu Thr Ser Gly Val His Thr Phe Pro Ala Val Leu Gln Ser Ser
             420                 425                 430
Gly Leu Tyr Ser Leu Ser Ser Val Val Asp Val Pro Ser Ser Ser Leu
             435                 440                 445
Gly Thr Gln Thr Tyr Ile Cys Asn Val Asn His Lys Pro Ser Asn Thr
```

```
                    450                 455                 460
Lys Val Asp Lys Arg Val Glu Pro Lys Ser Cys Asp Lys Thr His Thr
465                 470                 475                 480

Cys Pro Pro Cys Pro Ala Pro Glu Leu Leu Gly Gly Pro Ser Val Phe
                485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser His Glu Asp Pro Glu Val
                515                 520                 525

Lys Phe Asn Trp Tyr Val Asp Gly Val Glu Val His Asn Ala Lys Thr
            530                 535                 540

Lys Pro Arg Glu Glu Gln Tyr Asn Ser Thr Tyr Arg Val Val Ser Val
545                 550                 555                 560

Leu Thr Val Leu His Gln Asp Trp Leu Asn Gly Lys Glu Tyr Lys Cys
                565                 570                 575

Lys Val Ser Asn Lys Ala Leu Pro Ala Pro Ile Glu Lys Thr Ile Ser
            580                 585                 590

Lys Ala Lys Gly Gln Pro Arg Glu Pro Gln Val Tyr Thr Leu Pro Pro
            595                 600                 605

Ser Arg Glu Glu Met Thr Lys Asn Gln Val Ser Leu Thr Cys Leu Val
610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Lys Leu Thr Val Asp Lys Ser Arg Trp
            660                 665                 670

Gln Gln Gly Asn Val Phe Ser Cys Ser Val Met His Glu Ala Leu His
            675                 680                 685

Asn His Tyr Thr Gln Lys Ser Leu Ser Leu Ser Pro Gly Lys
            690                 695                 700

<210> SEQ ID NO 8
<211> LENGTH: 122
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
            115                 120
```

```
<210> SEQ ID NO 9
<211> LENGTH: 98
<212> TYPE: PRT
<213> ORGANISM: Artificial Sequence
<220> FEATURE:
<223> OTHER INFORMATION: CH1 of daratumumab

<400> SEQUENCE: 9

Ala Ser Thr Lys Gly Pro Ser Val Phe Pro Gln Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Val Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 10
<211> LENGTH: 118
<212> TYPE: PRT
<213> ORGANISM: Artificial Sequence
<220> FEATURE:
<223> OTHER INFORMATION: VH of atezolizumab

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 11
<211> LENGTH: 98
<212> TYPE: PRT
<213> ORGANISM: Artificial Sequence
<220> FEATURE:
<223> OTHER INFORMATION: CH1 of atezolizumab

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Asp Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 12
<211> LENGTH: 15
<212> TYPE: PRT
<213> ORGANISM: Homo sapiens

<400> SEQUENCE: 12

Glu Pro Lys Ser Cys Asp Lys Thr His Thr Cys Pro Pro Cys Pro
1               5                   10                  15

<210> SEQ ID NO 13
<211> LENGTH: 110
<212> TYPE: PRT
<213> ORGANISM: Homo sapiens

<400> SEQUENCE: 13

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 14
<211> LENGTH: 107
<212> TYPE: PRT
<213> ORGANISM: Homo sapiens

<400> SEQUENCE: 14

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
```

```
                    85                  90                  95

Thr Gln Lys Ser Leu Ser Leu Ser Pro Gly Lys
            100                 105

<210> SEQ ID NO 15
<211> LENGTH: 214
<212> TYPE: PRT
<213> ORGANISM: Artificial Sequence
<220> FEATURE:
<223> OTHER INFORMATION: LC daratumumab

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Thr Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Val
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 107
<212> TYPE: PRT
<213> ORGANISM: Homo sapiens

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Ckappa of daratumumab

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Thr Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Val Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 18
<211> LENGTH: 214
<212> TYPE: PRT
<213> ORGANISM: Artificial Sequence
<220> FEATURE:
<223> OTHER INFORMATION: LC atezolizumab

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ala Val Phe Ile Phe Pro Pro Ser Asp Glu Gln Leu Lys Ser Gly
        115                 120                 125

Thr Ala Ser Val Val Cys Leu Leu Lys Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 107
<212> TYPE: PRT
<213> ORGANISM: Artificial Sequence
<220> FEATURE:
<223> OTHER INFORMATION: VL atezolizumab

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Ckappa atezolizumab

<400> SEQUENCE: 20

Arg Thr Val Ala Ala Pro Ala Val Phe Ile Phe Pro Pro Ser Asp Glu
1               5                   10                  15

Gln Leu Lys Ser Gly Thr Ala Ser Val Val Cys Leu Leu Lys Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 21
<211> LENGTH: 19
<212> TYPE: PRT
<213> ORGANISM: Artificial Sequence
<220> FEATURE:
```

-continued

```
<223> OTHER INFORMATION: signal peptide

<400> SEQUENCE: 21

Met Asn Phe Gly Leu Arg Leu Ile Phe Leu Val Leu Thr Leu Lys Gly
1               5                   10                  15

Val Gln Cys
```

STABLE MULTISPECIFIC ANTIBODIES

CROSS-REFERENCE TO RELATED APPLICATION

This application is the U.S. national stage application of International Patent Application No. PCT/EP2018/057819, filed Mar. 27, 2018.

The Sequence Listing for this application is labeled "Seq-List.txt" which was created on Sep. 19, 2019 and is 24 KB. The entire content of the sequence listing is incorporated herein by reference in its entirety.

The invention relates to the production of multispecific antibody molecules, useful in medical field.

BACKGROUND OF THE INVENTION

Bispecific antibodies (bsAbs) combine specificities of two antibodies and simultaneously address different antigens or epitopes. BsAbs with 'two-targets' functionality can interfere with multiple surface receptors or ligands associated, for example with cancer, proliferation or inflammatory processes. BsAbs can also place targets into close proximity, either to support protein complex formation on one cell, or to trigger contacts between cells. Examples of 'forced-connection' functionalities are bsAbs that support protein complexation in the clotting cascade, or tumor-targeted immune cell recruiters and/or activators. Following years of research and development, the first bsAb was approved in 2009.

Initially, bispecific antibodies have been prepared by chemical conjugation, or by use of quadromas resulting from the fusion between two hybridoma cell lines producing two different mAbs. However, chemical conjugation may occasionally alter the antigen binding sites, resulting in an impairment of the biological properties of the antibody. The quadroma approach has the drawback that the random pairing of heavy and light chains from two different antibodies leads theoretically to ten equally possible combinations resulting in a mixture of immunoglobulin molecules, only one of which is the desired bispecific product, which has to be separated from the mispaired products.

Genetic engineering has now become the method of choice to produce bispecific antibodies and had led to the development of a wide variety of different recombinant bispecific antibody formats. Some of these bispecific antibodies are very simple and derive from single-chain Fv (scFv) fragments from two (or more) different antibodies, associated through an appropriate peptide linker. These antibodies are relatively easy to produce, and since they are formed by a single polypeptide chain and contain only the Fv regions of the parent antibodies, there is no problem of mispairing between chains. However, they are smaller than full-length immunoglobulins, and are devoid of constant regions, in particular of the Fc region. Although it may be advantageous in some applications, for instance when one wishes to avoid Fc-mediated effects, it is a disadvantage when Fc-mediated effector function is desired. Also, due to their small size and lack of Fc region, they have a very short half-life in vivo.

Therefore, other bispecific recombinant antibodies formats, mimicking more closely the naturally occurring immunoglobulin molecule, and in particular having a full Fc region, have been designed. They can be grouped into two main formats.

In the first one (IgG scFv), scFv fragments from an antibody A are fused to the ends (generally the C-terminal ends) of the heavy chains of an antibody B. The resulting antibody having only one type of heavy chain, which contains the VH, CH1, CH2 and CH3 domains of antibody B and the VH and VL domains of antibody A, and one type of light chain which contains the VL and CL domains of antibody B, mispairing between chains does not occur. Such a format is described for instance by Qu et al. (Blood, 111, 2211-2219, 2008).

In the second one, the heavy chain and the light chain from an antibody A are paired with the heavy chain and the light chain from an antibody B. This format reproduces the bispecific antibodies produced by the quadromas, and therefore raises similar problems of mispairing. To solve the problem of mispairing of the heavy chains, it has been proposed to mutate the CH3 domains of the antibodies in order to favor their heterodimerization (i.e. pairing of heavy chain A with heavy chain B) and to prevent their homodimerization. This was done by the so-called "knob into holes" approach (Ridgway et al, Protein Eng, 9, 617-21, 1996; U.S. Pat. No. 7,695,936). A "knob" mutation consisting in the replacement of a small amino-acid by a larger one is introduced at the CH3 dimer interface of the heavy chain of antibody A, resulting in a steric hindrance which prevents homodimerization. Concurrently in order to promote heterodimerization, a complementary "hole" mutation consisting in the replacement of a large amino acid by a smaller one is introduced into the CH3 domain of antibody B. To solve the problem of the heavy chain/light chain mispairing, it has been proposed to use antibodies of different specificities but sharing a common light chain, previously identified from an scFv phage library (Merchant et al., Nat Biotechnol, 16, 677-81, 1998; U.S. Pat. No. 7,183,076). The drawback of this approach is the difficulty in identifying antibodies having a common light chain. International patent application WO2013/005194 proposed that it was possible to prevent heavy chain/light chain mispairing and thus to ensure the desired matching of the chains by mutating some key residues at the interface of the CH1 and CL domains.

SUMMARY OF THE INVENTION

The inventors have now found that a new set of mutations could further improve matching of the chains in a multispecific antibody molecule.

The invention relates to multispecific, e.g. bispecific, antibody constructs comprising different Fab fragments having a particular set of mutations at the interface of the CH1 and CL domains, said mutations facilitate cognate pairing of heavy chain/light chain and preventing their mispairing.

Sequence position numbers used herein for the CH1 and CL domains refer to Kabat numbering (Kabat, E. A. et al., Sequences of proteins of immunological interest. 5th Edition—US Department of Health and Human Services, NIH publication no 91-3242, pp 662,680,689, 1991).

It is herein provided a mutated Fab fragment selected among:
a) a Fab fragment consisting of:
   the VH and VL domains of an antibody of interest;
   a CH1 domain which is derived from the CH1 domain of an immunoglobulin by substitution of the threonine residue at position 192 of said CH1 domain with an aspartic acid; and
   a CL domain which is derived from the CL domain of an immunoglobulin by substitution of the asparagine residue at position 137 of said CL domain with a lysine residue and substitution of the serine residue at position 114 of said CL domain with an alanine residue; and b) a Fab fragment consisting of:
   the VH and VL domains of an antibody of interest;
   a CH1 domain which is derived from the CH1 domain of an immunoglobulin by substitution of the leucine residue at position 124 of said CH1 domain with a glutamine and substitution of the serine residue at position 188 of said CH1 domain with a valine residue; and
   a CL domain which is derived from the CL domain of an immunoglobulin by substitution of the valine residue at position 133 of said CL domain with a threonine residue and substitution of the serine residue at position 176 of said CL domain with a valine residue.

Any construct, preferably any protein construct, comprising such mutated Fab fragment, is part of the present invention.

In particular it is provided a multispecific antigen-binding fragment comprising at least two Fab fragments with different CH1 and CL domains, wherein each Fab fragment recognizes a different epitope of interest, and said Fab fragments are tandemly arranged in any order, the C-terminal end of the CH1 domain of a first Fab fragment being linked to the N-terminal end of the VH domain of the following Fab fragment through a polypeptide linker,
wherein at least one Fab fragment, and more preferably two fragments, are selected from the group consisting of
a) a Fab fragment consisting of
   the VH and VL domains of an antibody;
   a CH1 domain which is derived from the CH1 domain of an immunoglobulin by substitution of the threonine residue at position 192 of said CH1 domain with an aspartic acid; and
   a CL domain which is derived from the CL domain of an immunoglobulin by substitution of the asparagine residue at position 137 of said CL domain with a lysine residue and substitution of the serine residue at position 114 of said CL domain with an alanine residue; and
b) a Fab fragment consisting of:
   the VH and VL domains of an antibody;
   a CH1 domain which is derived from the CH1 domain of an immunoglobulin by substitution of the leucine residue at position 124 of said CH1 domain with a glutamine and substitution of the serine residue at position 188 of said CH1 domain with a valine residue; and
   a CL domain which is derived from the CL domain of an immunoglobulin by substitution of the valine residue at position 133 of said CL domain with a threonine residue and substitution of the serine residue at position 176 of said CL domain with a valine residue.

According to a preferred embodiment, the CH1 domain is derived from an IgG immunoglobulin, advantageously of the IgG1 subtype. The CL domain is preferably a kappa type. Preferably, for use in human therapy, the immunoglobulin from which the mutated CH1 and mutated CL domains are derived is a human immunoglobulin.

The VH and VL domains can be derived from any antibody, native or genetically engineered, recognizing an epitope that one wishes to target.

The mutated Fab fragments of the invention can be used in any multispecific antibody construct where it is necessary to facilitate cognate pairing of heavy chain/light chain and prevent their mispairing.

Advantageously, the mutated Fab fragments may be used in a multispecific antibody molecule comprising antigen-binding fragments, each of which consists essentially of tandemly arranged Fab fragments, separated by linkers.

Therefore, another object of the invention is a multispecific antigen-binding fragment, comprising at least two, and up to six, different Fab fragments selected among:
   a Fab fragment (herein also defined as a: "wild-type Fab fragment") comprising wild-type CH1 and CL domains of an immunoglobulin;
   a mutated Fab fragment (a) as defined above;
   a mutated Fab fragment (b) as defined above;
   each Fab fragment recognizing a different epitope of interest and said Fab fragments being tandemly arranged in any order, the C-terminal end of the CH1 domain of a first one Fab fragment being linked to the N-terminal end of the VH domain of the following Fab fragment through a polypeptide linker;
   or one or two Fab fragments being tandemly arranged in any order and linked through a polypeptide linker to the C-terminus of the CH3 domain, or the C-terminus of a hinge sequence, while another Fab, or two tandemly arranged Fabs in any order, are attached to the N-terminus of a hinge sequence.

The above hinge sequence is typically a natural hinge sequence obtained from IgG1, IgG2, IgG3, IgG4, IgA1, IgA2, or IgD, and most preferably from the IgG1, or may be a modified sequence thereof through point mutations and/or additions of amino acid so that the modified hinge sequence consists of less than 80 amino acids, preferably less than 60 amino acids, still preferably less than 40 amino acids.

An "antigen-binding fragment" is defined herein as a molecule having two or more antigen-binding regions, each recognizing a different epitope. The different epitopes can be borne by a same antigenic molecule or by different antigenic molecules.

In a preferred embodiment, a multispecific antibody having two identical antigen-binding arms, each consisting of multispecific antigen-binding fragment, i.e. an antigen-binding fragment capable of binding multiple (i.e. more than one) antigens, as defined above, is further provided.

In a particular embodiment, the multispecific antibody has an immunoglobulin-like structure, and comprises
   two identical antigen-binding arms each consisting of such multispecific antigen-binding fragments as defined above;
   the dimerized CH2 and CH3 domains of an immunoglobulin;
   the hinge region of an IgA, IgG, or IgD, linking the C-terminal ends of CH1 domains of the antigen-binding arms to the N-terminal ends of the CH2 domains.

More particularly a subject of the invention is a multispecific, preferably bispecific, antibody comprising two heavy chains and four light chains, wherein each heavy chain comprises
   a Fc region of an immunoglobulin comprising Hinge-CH2-CH3 domains,
   which Fc region is linked to Fab heavy chain CH1-VH of antibody 1 (Ab1) by said Hinge domain,
   which in turn is linked to Fab heavy chain CH1-VH of antibody 2 (Ab2) by a polypeptide linker sequence, and the polypeptide linker sequence links the N-terminus of said Fab heavy chain VH domain of Ab1 with the C-terminus of said CH1 domain of Ab2, and the four light chains comprise Fab light chains CL-VL of Ab1 and Fab light chains CL-VL of Ab2 associated with their cognate heavy chain domains;

wherein Ab1 and Ab2 recognize different epitopes, and wherein the Fab CH1 domain of one of Ab1 or Ab2 is a mutated domain that derives from the CH1 domain of an immunoglobulin by substitution of the threonine residue at position 192 of said CH1 domain with an aspartic acid and the cognate CL domain is a mutated domain that derives from the CL domain of an immunoglobulin by substitution of the asparagine residue at position 137 of said CL domain with a lysine residue and substitution of the serine residue at position 114 of said CL domain with an alanine residue, and/or wherein the Fab CH1 domain of one or the other of Ab1 or Ab2 is a mutated domain that derives from the CH1 domain of an immunoglobulin by substitution of the leucine residue at position 124 of said CH1 domain with a glutamine and substitution of the serine residue at position 188 of said CH1 domain with a valine residue, and the cognate CL domain is a mutated domain that derives from the CL domain of an immunoglobulin by substitution of the valine residue at position 133 of said CL domain with a threonine residue and substitution of the serine residue at position 176 of said CL domain with a valine residue.

It is further described any protein chain selected among:
a light chain of a mutated Fab fragment of the invention;
a heavy chain of a mutated Fab fragment of the invention;
a heavy chain of an antigen-binding fragment of the invention;
a heavy chain of an immunoglobulin-like multispecific antibody of the invention.

The disclosure further provides a polynucleotide comprising a sequence encoding a protein chain of the invention. Said polynucleotide may also comprise additional sequences: in particular it may advantageously comprise a sequence encoding a leader sequence or signal peptide allowing secretion of said protein chain.

LEGEND TO THE FIGURES

Figure 4A:
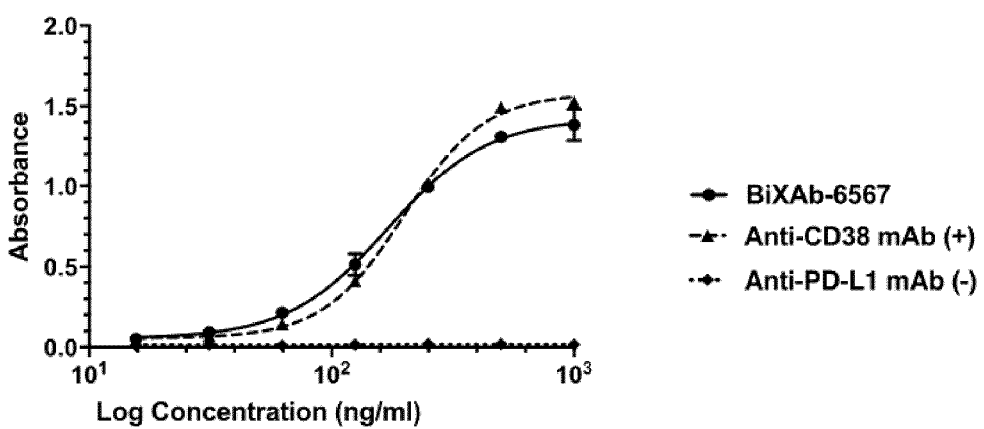
Figure 4B:
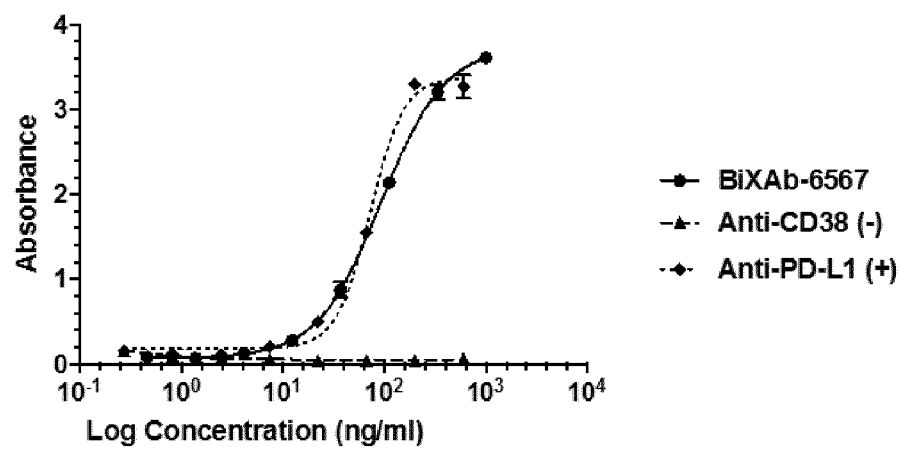
Figure 4C:
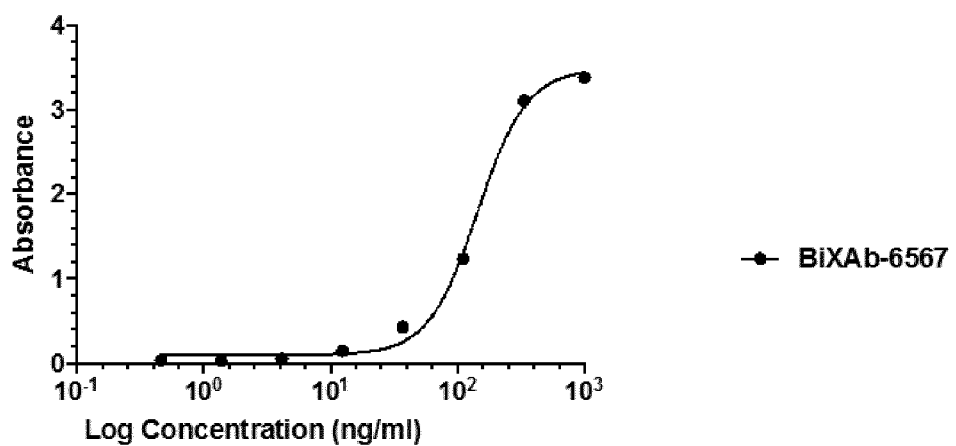

FIG. 4A shows the binding profiles of the two parental antibodies (anti-CD38 and anti-PD-L1) and BiXAb-6567 in a direct CD38 antigen binding ELISA. FIG. 4B shows the binding profiles of the two parental antibodies (anti-CD38 and anti-PD-L1) and BiXAb-6567 in a direct PD-L1 antigen binding ELISA. FIG. 4C shows the binding profile of BiXAb-6567 in a dual antigen (PD-L1 and CD38) binding ELISA.

Figure 5A:
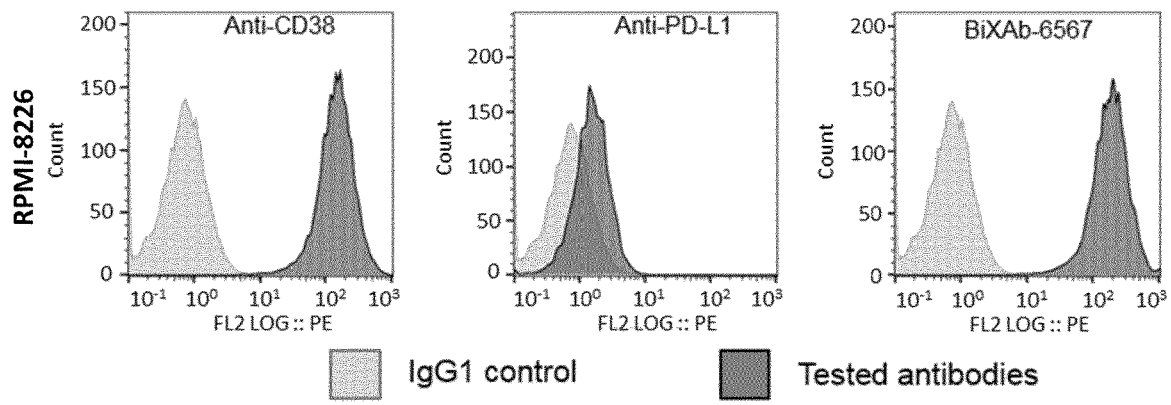
Figure 5B:
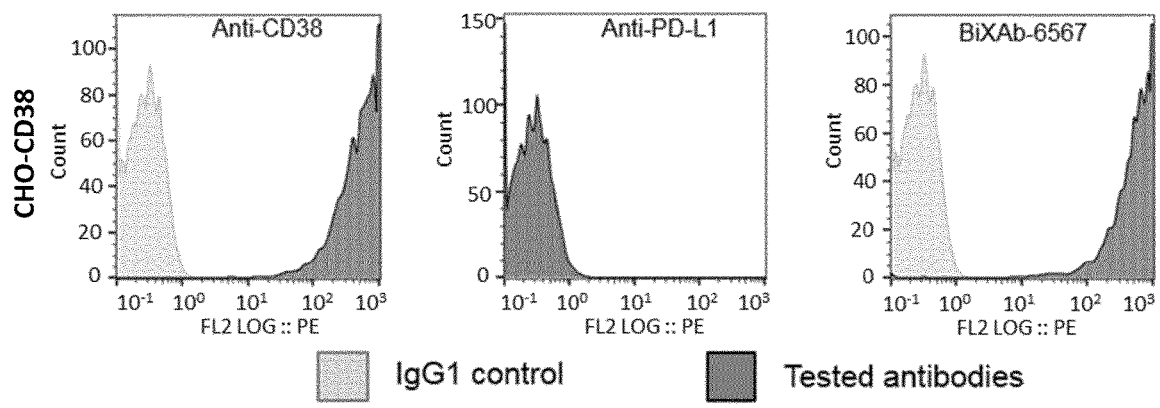
Figure 5C:
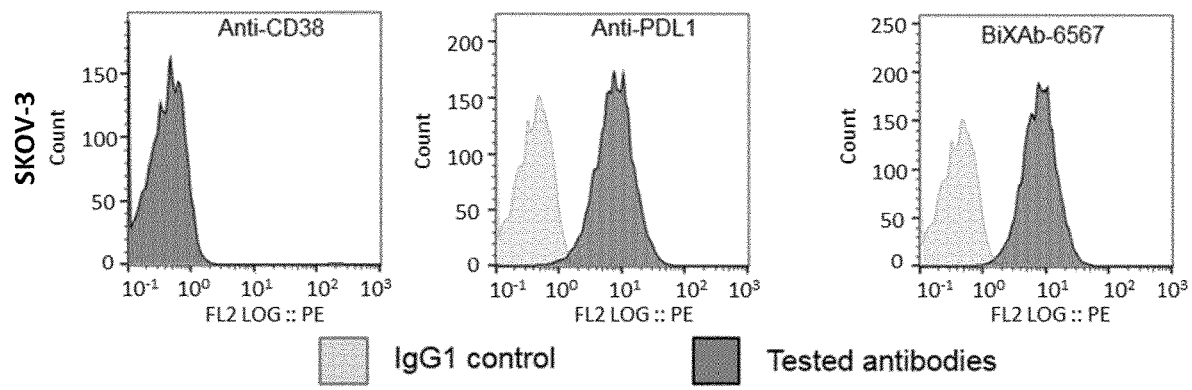

FIGS. 5A to 5C show Fluorescence-activated cell sorting profiles of the two parental mAbs (anti-CD38 and anti-PD-L1) and BiXAb-6567 on three different cell lines, 5A: multiple myeloma RPMI-8226, 5B: CHO cells stably transfected with full-length CD38, and 5C: ovarian cancer cell line SKOV-3.

Figure 6:
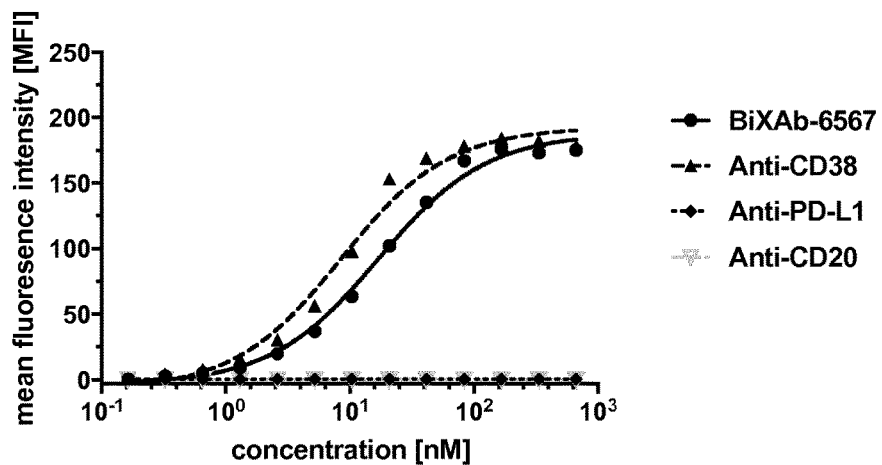

FIG. 6 shows the titration binding profiles on the CHO-CD38 cell line of the two parental antibodies (anti-CD38 and anti-PD-L1), BiXAb-6567, and the negative control anti-CD20 antibody.

Figure 7:
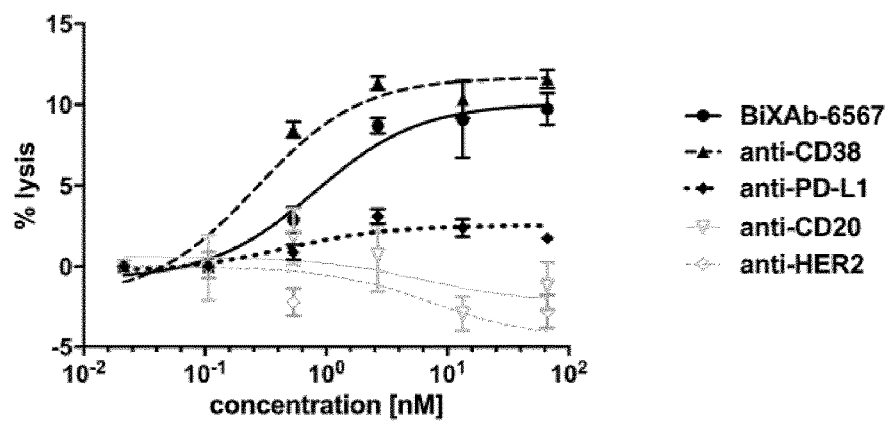

FIG. 7 shows the cytotoxic activity profiles of the two parental antibodies (anti-CD38 and anti-PD-L1), BiXAb-6567, and two negative control antibodies, anti-CD20 and anti-HER2, in an ADCC assay employing a multiple myeloma cell line, RPMI-8226, as target cells and unfractionated non-pre-activated mononuclear cells as effector cells.

Figure 8:
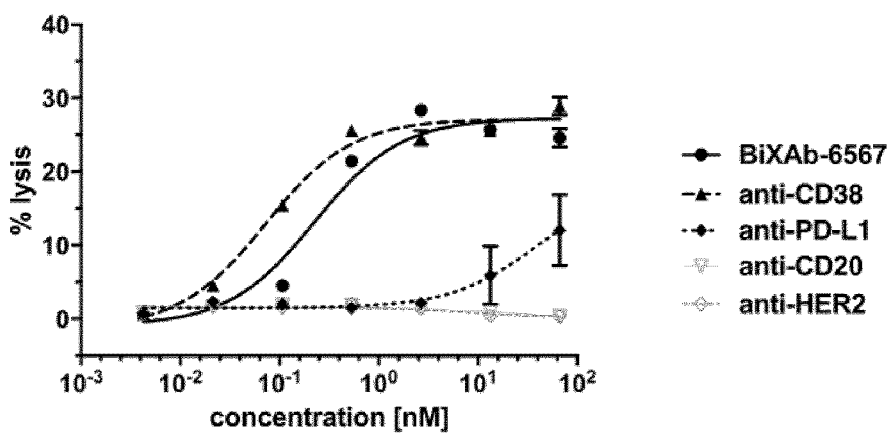

FIG. 8 shows the cytotoxic activity profiles of the two parental antibodies (anti-CD38 and anti-PD-L1), BiXAb-6567, and two negative control antibodies, anti-CD20 and anti-HER2, in an ADCC assay with the CHO-CD38 cell line as target cells and unfractionated non-pre-activated mononuclear cells as effector cells.

Figure 9:
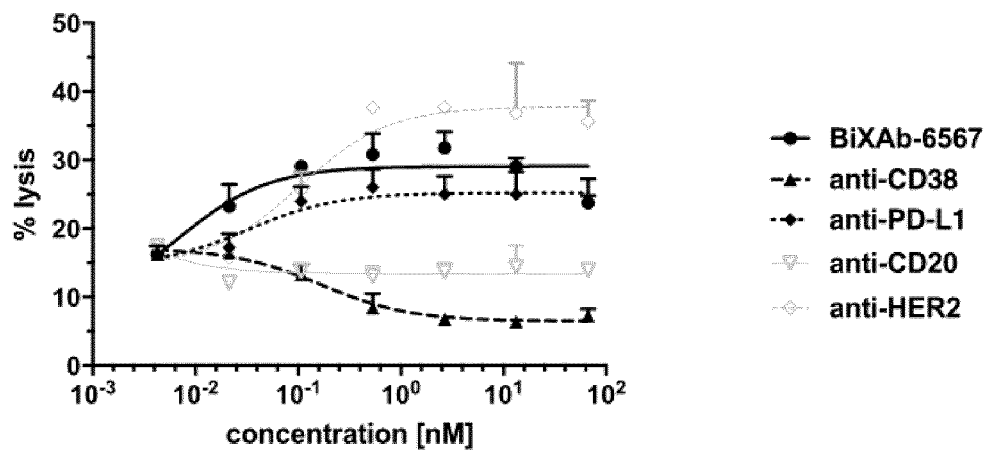

FIG. 9 shows the cytotoxic activity profiles of the two parental antibodies (anti-CD38 and anti-PD-L1), BiXAb-6567, and two negative control antibodies, anti-CD20 and anti-HER2, in an ADCC assay with the SKOV-3 cell line as target cells and enriched IL-12 pre-activated NK cells as effector cells.

Figure 10:
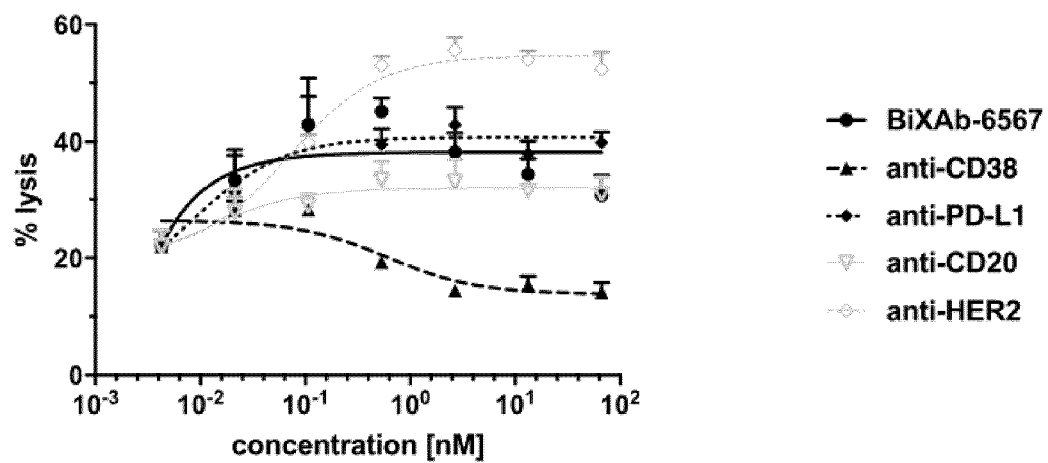

FIG. 10 shows the cytotoxic activity profiles of the two parental antibodies (anti-CD38 and anti-PD-L1), BiXAb-6567, and two negative control antibodies, anti-CD20 and anti-HER2, in an ADCC assay with the SKOV-3 cell line as target cells and enriched IL-15 pre-activated NK cells as effector cells.

Figure 11:
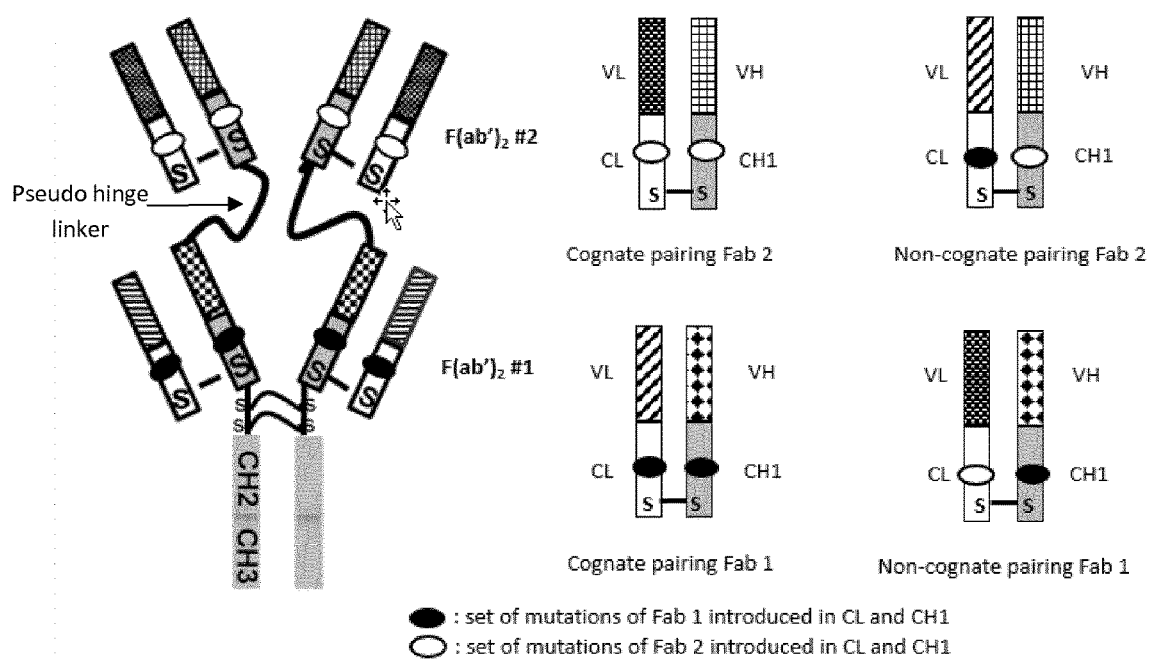

FIG. 11 is a schematic representation of a bispecific antibody of the invention, comprising two heavy chains, and four light chains, and showing different combinations of mutations.

DETAILED DESCRIPTION

Definitions

The basic structure of a naturally occurring antibody molecule is a Y-shaped tetrameric quaternary structure consisting of two identical heavy chains and two identical light chains, held together by non-covalent interactions and by inter-chain disulfide bonds.

In mammalian species, there are five types of heavy chains: α, δ, ε, γ, and μ, which determine the class (isotype) of immunoglobulin: IgA, IgD, IgE, IgG, and IgM, respectively. The heavy chain N-terminal variable domain (VH) is followed by a constant region, containing three domains (numbered CH1, CH2, and CH3 from the N-terminus to the C-terminus) in heavy chains γ, α, and δ, while the constant region of heavy chains μ and ε is composed of four domains (numbered CH1, CH2, CH3 and CH4 from the N-terminus to the C-terminus). The CH1 and CH2 domains of IgA, IgG, and IgD are separated by a flexible hinge, which varies in length between the different classes and in the case of IgA and IgG, between the different subtypes: IgG1, IgG2, IgG3, and IgG4 have respectively hinges of 15, 12, 62 (or 77), and 12 amino acids, and IgA1 and IgA2 have respectively hinges of 20 and 7 amino acids.

There are two types of light chains: λ and κ, which can associate with any of the heavy chains isotypes, but are both of the same type in a given antibody molecule. Both light chains appear to be functionally identical. Their N-terminal variable domain (VL) is followed by a constant region consisting of a single domain termed CL.

The heavy and light chains pair by protein/protein interactions between the CH1 and CL domains, and via VH NL interactions and the two heavy chains associate by protein/protein interactions between their CH3 domains. The structure of the immunoglobulin molecule is generally stabilized by interchain disulfide bonds between the CH1 and CL domains and between the hinges.

The antigen-binding regions correspond to the arms of the Y-shaped structure, which consist each of the complete light chain paired with the VH and CH1 domains of the heavy chain, and are called the Fab fragments (for Fragment antigen binding). Fab fragments were first generated from native immunoglobulin molecules by papain digestion, which cleaves the antibody molecule in the hinge region, on the amino-terminal side of the interchain disulfide bonds, thus releasing two identical antigen-binding arms. Other proteases such as pepsin, also cleave the antibody molecule in the hinge region, but on the carboxy-terminal side of the interchain disulfide bonds, releasing fragments consisting of two identical Fab fragments and remaining linked through disulfide bonds; reduction of disulfide bonds in the F(ab')2 fragments generates Fab' fragments.

The part of the antigen-binding region corresponding to the VH and VL domains is called the Fv fragment (for Fragment variable); it contains the CDRs (complementarity determining regions), which form the antigen-binding site (also termed paratope).

The effector region of the antibody which is responsible of its binding to effector molecules or cells, corresponds to the stem of the Y-shaped structure, and contains the paired CH2 and CH3 domains of the heavy chain (or the CH2, CH3 and CH4 domains, depending on the class of antibody), and is called the Fc (for Fragment crystallizable) region.

Due to the identity of the two heavy chains and the two light chains, naturally occurring antibody molecules have two identical antigen-binding sites and thus bind simultaneously to two identical epitopes.

In the context of the invention, the "multispecific antigen-binding fragment" is defined herein as a molecule having two or more antigen-binding regions, each recognizing a different epitope. The different epitopes can be borne by a same antigenic molecule or by different antigenic molecules. The term "recognizing" or "recognizes" means that the fragment specifically binds a target antigen.

A "multispecific antibody" is comprised of at least two multispecific antigen-binding fragments/arms and is capable of binding two, three or more different antigens.

An antibody "specifically binds" to a target antigen if it binds with greater affinity, avidity, more readily, and/or with greater duration than it binds to other substances. "Specific binding" or "preferential binding" does not necessarily require (although it can include) exclusive binding. Generally, but not necessarily, reference to binding means preferential binding.

The term "mutated derivative", "mutant", or "functional variant" designates a sequence that differs from the parent sequence to which it refers by deletion, substitution or insertion of one or several amino acids. Preferably the mutated derivative preferably shows at least 80%, preferably at least 85%, still preferably at least 90% homology sequence with the native sequence. In a particular embodiment, the mutations do not substantially impact the function of the antibody.

Mutated derivatives, or functional variants, can comprise a VH chain that comprises an amino acid sequence at least 85% (e.g., 90%, 92%, 94%, 95%, 96%, 97%, 98%, or 99%) identical to any of the reference sequences recited herein, a VL chain that has an amino acid sequence at least 85% (e.g., 90%, 92%, 94%, 95%, 96%, 97%, 98%, or 99%) identical to any of the reference sequences recited herein, or both. These variants are capable of binding to the target antigens. In some examples, the variants possess similar antigen-binding affinity relative to the reference antibodies described above (e.g., having a KD less than $1\times10^{-7}$ M, $10^{-8}$ M, preferably less than $1\times10^{-9}$ or $1\times10^{-10}$ M).

The affinity of the binding is defined by the terms ka (associate rate constant), kd (dissociation rate constant), or KD (equilibrium dissociation). Typically, specifically binding when used with respect to an antibody refers to an antibody that specifically binds to ("recognizes") its target(s) with an affinity (KD) value less than $10^{-7}$ M, preferably less than $10^{-8}$ M, e.g., less than $10^{-9}$ M or $10^{-10}$ M. A lower KD value represents a higher binding affinity (i.e., stronger binding) so that a KD value of $10^{-9}$ indicates a higher binding affinity than a KD value of $10^{-8}$.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other embodiments, the functional variants described herein can contain one or more mutations (e.g., conservative substitutions), which preferably do not occur at residues, which are predicted to interact with one or more of the CDRs.

It is herein described mutated derivatives, or functional variants, which are substantially identical to the reference antibody.

The term "substantially identical" or "insubstantial" means that the relevant amino acid sequences (e.g., in framework regions (FRs), CDRs, VH, or VL domain) of a variant differ insubstantially (e.g., including conservative amino acid substitutions) as compared with a reference antibody such that the variant has substantially similar binding activities (e.g., affinity, specificity, or both) and bioactivities relative to the reference antibody. Such a variant may include minor amino acid changes, e.g. 1 or 2 substitutions in a 5 amino acid sequence of a specified region. Generally, more substitutions can be made in FR regions, in contrast to CDR regions, as long as they do not adversely impact the binding function of the antibody (such as reducing the binding affinity by more than 50% as compared to the original antibody). In some embodiment, the sequence identity can be about 85%, 90%, 95%, 96%, 97%, 98%, 99% or higher, between the original and the modified antibody. In some embodiments, the modified antibody has the same binding specificity and has at least 50% of the affinity of the original antibody.

Conservative substitutions will produce molecules having functional and chemical characteristics similar to those of the molecule from which such modifications are made. For example, a "conservative amino acid substitution" may involve a substitution of a native amino acid residue with another residue such that there is little or no effect on the polarity or charge of the amino acid residue at that position. Desired amino acid substitutions (whether conservative or non-conservative) can be determined by those skilled in the art. For example, amino acid substitutions can be used to identify important residues of the molecule sequence, or to increase or decrease the affinity of the molecules described herein. Variants comprising one or more conservative amino acid substitutions can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Amino acid sequence variants of the antibody can be prepared by introducing appropriate nucleotide changes into the antibody nucleic acid, or via peptide synthesis. Such modifications include, for example, deletions from, and/or insertions into and/or substitutions of, residues within the amino acid sequences of the antibody. Any combination of deletion, insertion, and substitution is made to achieve the final construct, provided that the final construct possesses the desired characteristics. Nucleic acid molecules encoding amino acid sequence variants of the antibody can be prepared by a variety of methods known in the art. These methods include, but are not limited to, oligonucleotide-mediated (or site-directed) mutagenesis, PCR mutagenesis, and cassette mutagenesis of an earlier prepared variant or a non-variant (natural) version of the antibody. In one embodiment, the equilibrium dissociation constant (KD) value of the antibodies of the invention is less than $10^{-7}$ M, particularly less than $10^{-8}$ M, $10^{-9}$ M or $10^{-10}$ M. The binding affinity may be determined using techniques known in the art, such as ELISA or biospecific interaction analysis (e.g. using surface plasmon resonance), or other techniques known in the art.

Any of the molecules described herein can be examined to determine their properties, such as antigen-binding activity, antigen-binding specificity, and biological functions, following routine methods.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

The term "treatment" or "treating" refers to an action, application or therapy, wherein a subject, including a human being, is subjected to medical aid with the purpose of improving the subject's condition, directly or indirectly. Particularly, the term refers to reducing incidence, or alleviating symptoms, eliminating recurrence, preventing recurrence, preventing incidence, improving symptoms, improving prognosis or combination thereof in some embodiments. The skilled artisan would understand that treatment does not necessarily result in the complete absence or removal of symptoms. For example, with respect to cancer, "treatment" or "treating" may refer to slowing neoplastic or malignant cell growth, proliferation, or metastasis, preventing or delaying the development of neoplastic or malignant cell growth, proliferation, or metastasis, or some combination thereof.

Design of the Preferred Multispecific Antibodies

It is herein provided multispecific antigen-binding fragment(s) and multispecific antibody constructs, comprising said fragments, wherein each multispecific antigen-binding fragment consists essentially of tandemly arranged Fab fragments, separated by the linker of the invention.

Such fragments and constructs preferably comprise chains from human immunoglobulins, preferably IgG, still preferably IgG1.

In case of a multispecific antigen-binding fragment comprising more than two different Fab fragments, the polypeptide linkers separating the Fab fragments can be identical or different. According to a preferred embodiment of a multispecific antibody of the invention, it has two identical antigen-binding arms, each consisting of antigen-binding fragments capable of binding multiple (more than one) antigens, as defined above. The antigen-binding arms can be linked together in diverse ways, depending on the intended use for the antibody.

If one wishes to obtain an antibody without Fc-mediated effects, the antibody will comprise no Fc region. In this case, the two antigen-binding arms can be linked together for instance:

by homodimerization of the antigen-binding arms through the inter-chain disulfide bonds provided by the polypeptide linker(s) separating the Fab fragments if said linker(s) contain cysteine residues; and/or through the addition at the C-terminal end of each antigen-binding arm, of a polypeptide extension containing cysteine residues allowing the formation of inter-chain disulfide bonds, and homodimerization of said polypeptide extension resulting in a hinge-like structure; by way on non-limitative examples, said polypeptide extension may be for instance a hinge sequence of an IgG1, IgG2, IgG3, IgA, or IgD;

through a semi-rigid linker joining the C-terminal ends of the heavy chains of the two antigen-binding arms to form a single polypeptide chain and maintaining said antigen-binding arms at a sufficient distance from each other.

Alternatively, if effector functions such as antibody-dependent cell-mediated cytotoxicity (ADCC), antibody-dependent phagocytosis (ADP), and complement-dependent cytotoxicity (CDC), are desired, a multispecific antibody of the invention can further comprise a Fc domain providing these effector functions. The choice of the Fc domain will depend on the type of desired effector functions.

In this case, a multispecific antibody of the invention has an immunoglobulin-like structure, comprising:

two identical multispecific antigen-binding arms as defined above;

the dimerized CH2 and CH3 domains of an immunoglobulin;

either the hinge region of an IgA, IgG, or IgD, linking the C-terminal ends of the CH1 domains of the antigen-binding arms to the N-terminal ends of the CH2 domains, or alternatively, when the CH4 domains that follow the CH3 domains come from an IgM or IgE, the C-terminal ends of the CH1 domains of the antigen-binding arms, in this case, can be linked directly to the N-terminal ends of the CH2 domains.

Preferably, the CH2 and CH3 domains, the hinge region and/or the CH4 domains are derived from a same immunoglobulin or from immunoglobulins of the same isotype and subclass as the CH1 domains of the antigen-binding arm.

The CH2, CH3, and optionally CH4 domains, as well as the hinge regions from native immunoglobulins can be used. It is also possible to mutate them, if desired, for instance in order to modulate the effector function of the antibody. In some instances, whole or part of the CH2 or the CH3 domain can be omitted.

The invention more particularly provides multispecific, preferably bispecific tetravalent antibodies, comprising two binding sites to each of their targets, and a functional Fc domain allowing the activation of effector functions such as antibody-dependent cell-mediated cytotoxicity (ADCC), phagocytosis, and complement-dependent cytotoxicity (CDC).

Such preferred antibodies of the invention are full-length antibodies. They preferably comprise heavy chains and light chains from human immunoglobulins, preferably IgG, still preferably IgG1.

The light chains may be lambda or kappa light chains, they preferably are kappa light chains.

In a preferred embodiment, the polypeptide linker used in the invention connects two pairs of IgG Fab domains in a tetra-Fab multispecific, preferably bispecific, antibody format, the amino acid sequence of which comprises the heavy chain sequences of at least two Fab joined by the polypeptide linker, followed by the native hinge sequence, followed by the IgG Fc sequence, co-expressed with the appropriate IgG light chain sequences.

An example of the preferred bispecific antibodies of the invention, which have an IgG-like structure, is illustrated in FIG. 11.

In a preferred embodiment, the bispecific antibodies of the invention typically comprise
- a continuous heavy chain constructed of an Fc (Hinge-CH2-CH3),
- followed by antibody 1 Fab heavy chain (CH1-VH) and the successive Fab heavy chain (CH1-VH) of antibody 2, the latter joined by a hinge-derived polypeptide linker sequence,
- and during protein expression the resulting heavy chain assembles into dimers while the co-expressed antibody 1 and antibody 2 light chains (VL-CL) associate with their cognate heavy chains in order to form the final tandem F(ab)'2-Fc molecule,
- the antibody 1 (Ab1) and the antibody 2 (Ab2) being different.

In a preferred embodiment, it is described bispecific antibodies, which comprise
- two Fab fragments with different mutated CH1 and mutated CL domains consisting of
  a) Fab fragment having mutated CH1 and mutated C-Kappa domains derived from a human IgG1/Kappa, and the VH and VL domains of Ab1,
  b) Fab fragment having mutated CH1 and mutated C-Kappa domains derived from a human IgG1/Kappa and the VH and VL domains of Ab2,
  c) a mutated light chain constant domain, which is derived from human Kappa constant domain,
- the Fab fragments being tandemly arranged in the following order
  the C-terminal end of the mutated CH1 domain of Ab1 Fab fragment being linked to the N-terminal end of the VH domain of Ab2 Fab fragment through a polypeptide linker,
  the hinge region of a human IgG1 linking the C-terminal ends of mutated CH1 domain of Ab2 fragment to the N-terminal of the CH2 domain,
  the dimerized CH2 and CH3 domains of a human IgG1.

Ab1 and Ab2 may be any antibody of interest, especially any antibody of therapeutic interest.

In a particular embodiment, Ab1 and Ab2, being different, independently are selected from the group consisting of anti-CD38 antibody (such as daratumumab) and an anti-PD-L1 antibody (such as atezolizumab).

In another particular embodiment, Ab1 and Ab2, being different, independently are selected from the group consisting of an anti-EGFR antibody and an anti-HER2/neu receptor. In a preferred embodiment, Ab1 and Ab2, being different, independently are selected from the group consisting of cetuximab or a mutated derivative thereof, on the one hand, and trastuzumab, or a mutated derivative thereof, on the other hand.

Such antibodies are useful as a medicament, more particularly in treating a cancer.

In a particular example, the bispecific molecule is a bispecific anti-CD38, anti-PD-L1 antibody which comprises, preferably consists of, a) two heavy chains, each comprising, preferably consisting of, SEQ ID NO:7 and b) four light chains, two comprising, preferably consisting of, SEQ ID NO:15, the two others comprising, preferably consisting of, SEQ ID NO: 18. Such bispecific antibody is designated BiXAb-6567.

```
SEQ ID NO: 7 (heavy chain) is:
EVQLLESGGGLVQPGGSLRLSCAVSGFTFNSFAMSWVRQAPGKGLEW

VSAISGSGGGTYYADSVKGRFTISRDNSKNTLYLQMNSLRAEDTAVY

FCAKDKILWFGEPVFDYWGQGTLVTVSSASTKGPSVFPQAPSSKSTS

GGTAALGCLVKDYFPEPVTVSWNSGALTSGVHTFPAVLQSSGLYSLV

SVVTVPSSSLGTQTYICNVNHKPSNTKVDKRVEPKSCDKTHTSPPAP

APELLGGPAAPPAPAPAGGEVQLVESGGGLVQPGGSLRLSCAASGFT

FSDSWIHWVRQAPGKGLEWVAWISPYGGSTYYADSVKGRFTISADTS

KNTAYLQMNSLRAEDTAVYYCARRHWPGGFDYWGQGTLVTVSSASTK

GPSVFPLAPSSKSTSGGTAALGCLVKDYFPEPVTVSWNSGALTSGVH

TFPAVLQSSGLYSLSSVVDVPSSSLGTQTYICNVNHKPSNTKVDKRV

EPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVL

HQDWLNGKEYKCKVSNKALPAPIEKTISKAKGQPREPQVYTLPPSRE

EMTKNQVSLTCLVKGFYPSDIAVEWESNGQPENNYKTTPPVLDSDGS

FFLYSKLTVDKSRWQQGNVFSCSVMHEALHNHYTQKSLSLSPGK

This heavy chain sequence comprises
VH of daratumumab
                                    (SEQ ID NO: 8)
EVQLLESGGGLVQPGGSLRLSCAVSGFTFNSFAMSWVRQAPGKGLEW

VSAISGSGGGTYYADSVKGRFTISRDNSKNTLYLQMNSLRAEDTAVY

FCAKDKILWFGEPVFDYWGQGTLVTVSS

CH1 domain (human IgG1 of G1m(3) allotype with
mutations L124Q and S188V) of daratumumab Fab
                                    (SEQ ID NO: 9)
ASTKGPSVFPQAPSSKSTSGGTAALGCLVKDYFPEPVTVSWNSGALT

SGVHTFPAVLQSSGLYSLVSVVTVPSSSLGTQTYICNVNHKPSNTKV

DKRV
```

```
AP linker
                                        (SEQ ID NO: 3)
EPKSCDKTHTSPPAPAPELLGGPAAPPAPAPAGG VH of atezolizumab
                                       (SEQ ID NO: 10)
EVQLVESGGGLVQPGGSLRLSCAASGFTFSDSWIHWVRQAPGKGLEW

VAWISPYGGSTYYADSVKGRFTISADTSKNTAYLQMNSLRAEDTAVY

YCARRHWPGGFDYWGQGTLVTVSS

CH1 domain (human IgG1 of G1m(3) allotype with
mutation T192D of Fab atezolizumab
                                       (SEQ ID NO: 11)
ASTKGPSVFPLAPSSKSTSGGTAALGCLVKDYFPEPVTVSWNSGALT

SGVHTFPAVLQSSGLYSLSSVVDVPSSSLGTQTYICNVNHKPSNTKV

DKRV

Hinge of human IgG1
                                       (SEQ ID NO: 12)
EPKSCDKTHTCPPCP CH2 domain of human IgG1
                                       (SEQ ID NO: 13)
APELLGGPSVFLFPPKPKDTLMISRTPEVTCVVVDVSHEDPEVKFNW

YVDGVEVHNAKTKPREEQYNSTYRVVSVLTVLHQDWLNGKEYKCKVS

NKALPAPIEKTISKAK

CH3 domain of human IgG1 of G1m(3) allotype
                                       (SEQ ID NO: 14)
GQPREPQVYTLPPSREEMTKNQVSLTCLVKGFYPSDIAVEWESNGQP

ENNYKTTPPVLDSDGSFFLYSKLTVDKSRWQQGNVFSCSVMHEALHN

HYTQKSLSLSPGK

Light chain SEQ ID NO: 15 (daratumumab) is
EIVLTQSPATLSLSPGERATLSCRASQSVSSYLAWYQQKPGQAPRLL

IYDASNRATGIPARFSGSGSGTDFTLTISSLEPEDFAVYYCQQRSNW

PPTFGQGTKVEIKRTVAAPSVFIFPPSDEQLKSGTASVTCLLNNFYP

REAKVQWKVDNALQSGNSQESVTEQDSKDSTYSLVSTLTLSKADYEK

HKVYACEVTHQGLSSPVTKSFNRGEC

This light chain sequence comprises
VL of daratumumab
                                       (SEQ ID NO: 16)
EIVLTQSPATLSLSPGERATLSCRASQSVSSYLAWYQQKPGQAPRLL

IYDASNRATGIPARFSGSGSGTDFTLTISSLEPEDFAVYYCQQRSNW

PPTFGQGTKVEIK

CKappa domain of daratumumab with mutations
V133T and S176V
                                       (SEQ ID NO: 17)
RTVAAPSVFIFPPSDEQLKSGTASVTCLLNNFYPREAKVQWKVDNAL

QSGNSQESVTEQDSKDSTYSLVSTLTLSKADYEKHKVYACEVTHQGL

SSPVTKSFNRGEC

Light chain SEQ ID NO: 18 (atezolizumab) is
DIQMTQSPSSLSASVGDRVTITCRASQDVSTAVAWYQQKPGKAPKLL

IYSASFLYSGVPSRFSGSGSGTDFTLTISSLQPEDFATYYCQQYLYH

PATFGQGTKVEIKRTVAAPAVFIFPPSDEQLKSGTASVVCLLKNFYP

REAKVQWKVDNALQSGNSQESVTEQDSKDSTYSLSSTLTLSKADYEK

HKVYACEVTHQGLSSPVTKSFNRGEC

This light chain sequence comprises
VL of atezolizumab
                                       (SEQ ID NO: 19)
DIQMTQSPSSLSASVGDRVTITCRASQDVSTAVAWYQQKPGKAPKLL

IYSASFLYSGVPSRFSGSGSGTDFTLTISSLQPEDFATYYCQQYLYH

PATFGQGTKVEIK

CKappa domain of atezolizumab with mutations
S114A and N137K
                                       (SEQ ID NO: 20)
RTVAAPAVFIFPPSDEQLKSGTASVVCLLKNFYPREAKVQWKVDNAL

QSGNSQESVTEQDSKDSTYSLSSTLTLSKADYEKHKVYACEVTHQGL

SSPVTKSFNRGEC
```

A third pair of Fab domains (directed against a different antigen target than the first and the second pairs of Fab domains) can also be linked with an identical or different polypeptide linker: i) either via the C-termini of the Heavy Chains of the said third pair of Fab domains to the N-termini of the Heavy Chains of the exterior (i.e. Fc-distal) Fab domains, ii) or via either the C- or the N-termini of the Heavy Chains of the said third pair of Fab domains to the C-termini of both Heavy Chains of the Fc-domain.

Any of the molecules described herein can be modified to contain additional non-proteinaceous moieties that are known in the art and readily available, e.g., by PEGylation or hyperglycosylation. Modifications that can enhance serum half-life or stability against proteolytic degradation are encompassed.

The antibodies of the invention may be glycosylated or not, or may show a variety of glycosylation profiles. In a preferred embodiment, antibodies are non-glycosylated on the variable region of the heavy chains, but are glycosylated on the Fc region.

One may use humanized forms of a reference non-human antibody. In a humanization approach, complementarity determining regions (CDRs) and certain other amino acids from donor variable regions are grafted into human variable acceptor regions and then joined to human constant regions. See, e.g. Riechmann et al., Nature 332:323-327 (1988); U.S. Pat. No. 5,225,539.

Another example of the constructs of the invention is a bispecific antigen-binding fragment Fab-Fab, which does not contain the Fc domain.

Such Fab-Fab constructs typically comprise two different Fab domains. Such antibodies possess only one Fab domain each that binds to antigen 1 and to antigen 2. They possess the same Light Chains as in the corresponding BiXAb antibodies; however, the Heavy Chain of Fab-Fabs is shortened in such a fashion so that their most C-terminal residue is Cysteine-220 (in EU numbering).

Another example of the constructs of the invention is a dimerized Fab-Fab construct (e.g. either via disulfide in the linker or via the natural disulfides of the hinge at the C terminus of the C-terminus-proximal Fab domain).

Design of the Linkers

The polypeptide linker, also designated "hinge-derived polypeptide linker sequence" or "pseudo hinge linker", comprises all or part of the sequence of the hinge region of one or more immunoglobulin(s) selected among IgA, IgG, and IgD, preferably of human origin. Said polypeptide linker may comprise all or part of the sequence of the hinge region of only one immunoglobulin. In this case, said immunoglobulin may belong to the same isotype and subclass as the immunoglobulin from which the adjacent CH1 domain is derived, or to a different isotype or subclass. Alternatively, said polypeptide linker may comprise all or part of the sequences of hinge regions of at least two immunoglobulins of different isotypes or subclasses. In this case, the N-terminal portion of the polypeptide linker, which directly follows the CH1 domain, preferably consists of all or part of the hinge region of an immunoglobulin belonging to the same isotype and subclass as the immunoglobulin from which said CH1 domain is derived.

Optionally, said polypeptide linker may further comprise a sequence of from 2 to 15, preferably of from 5 to 10 N-terminal amino acids of the CH2 domain of an immunoglobulin.

The polypeptide linker sequence typically consists of less than 80 amino acids, preferably less than 60 amino acids, still preferably less than 40 amino acids.

In some cases, sequences from native hinge regions can be used; in other cases, point mutations can be brought to these sequences, in particular the replacement of one or more cysteine residues in native IgG1, IgG2 or IgG3 hinge sequences by alanine or serine, in order to avoid unwanted intra-chain or inter-chains disulfide bonds.

In a particular embodiment, the polypeptide linker sequence comprises or consists of amino acid sequence EPKX$_1$CDKX$_2$HX$_3$X$_4$PPX$_5$PAPELLGGPX$_6$X$_7$PPX$_8$PX$_9$PX$_{10}$GG (SEQ ID NO:1), wherein X$_1$, X$_2$, X$_3$, X$_4$, X$_5$, X$_6$, X$_7$, X$_8$, X$_9$, X10, identical or different, are any amino acid. In particular, the polypeptide linker sequence may comprise or consist of a sequence selected from the group consisting of

```
                                            (SEQ ID NO: 2)
EPKSCDKTHTSPPAPAPELLGGPGGPPGPGPGGG;

(SEQ ID NO: 3)
EPKSCDKTHTSPPAPAPELLGGPAAPPAPAPAGG;

(SEQ ID NO: 4)
EPKSCDKTHTSPPAPAPELLGGPAAPPGPAPGGG;

(SEQ ID NO: 5)
EPKSCDKTHTCPPCPAPELLGGPSTPPTPSPSGG
and (SEQ ID NO: 6)
EPKSCDKTHTSPPSPAPELLGGPSTPPTPSPSGG.
```

In a particular embodiment, X$_1$, X$_2$ and X$_3$, identical or different, are Threonine (T) or Serine (S).

In another particular embodiment, X$_1$, X$_2$ and X3, identical or different, are selected from the group consisting of Ala (A), Gly (G), Val (V), Asn (N), Asp (D) and Ile (I), still preferably X$_1$, X2 and X$_3$, identical or different, may be Ala (A) or Gly (G).

Alternatively, X$_1$, X$_2$ and X$_3$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q).

In a particular embodiment, X$_4$ and X$_5$, identical or different, are any amino acid selected from the group consisting of Serine (S), Cysteine (C), Alanine (A), and Glycine (G).

In a preferred embodiment, X$_4$ is Serine (S) or Cysteine (C).

In a preferred aspect, X$_5$ is Alanine (A) or Cysteine (C).

In a particular embodiment, X$_6$, X$_7$, X$_8$, X$_9$, X$_{10}$, identical or different, are any amino acid other than Threonine (T) or Serine (S). Preferably X$_6$, X$_7$, X$_8$, X$_9$, X10, identical or different, are selected from the group consisting of Ala (A), Gly (G), Val (V), Asn (N), Asp (D) and Ile (I).

Alternatively, X$_6$, X$_7$, X$_8$, X$_9$, X$_{10}$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q). In a preferred embodiment, X$_6$, X$_7$, X$_8$, X$_9$, X$_{10}$, identical or different, are selected from the group consisting of Ala (A) and Gly (G).

In still a preferred embodiment, X6 and X7 are identical and are preferably selected from the group consisting of Ala (A) and Gly (G).

In a preferred embodiment, the polypeptide linker sequence comprises or consists of sequence SEQ ID NO: 1, wherein X$_1$, X$_2$ and X$_3$, identical or different, are Threonine (T), Serine (S);

X$_4$ is Serine (S) or Cysteine (C);

X$_5$ is Alanine (A) or Cysteine (C);

X$_6$, X$_7$, X$_8$, X$_9$, X$_{10}$, identical or different, are selected from the group consisting of Ala (A) and Gly (G).

In another preferred embodiment, the polypeptide linker sequence comprises or consists of sequence SEQ ID NO: 1, wherein X$_1$, X$_2$ and X$_3$, identical or different, are Ala (A) or Gly (G);

X$_4$ is Serine (S) or Cysteine (C);

X$_5$ is Alanine (A) or Cysteine (C);

X$_6$, X$_7$, X$_8$, X$_6$, X$_{10}$, identical or different, are selected from the group consisting of Ala (A) and Gly (G).

In case of a multispecific antigen-binding fragment, comprising more than two different Fab fragments, the polypeptide linkers separating the Fab fragments can be identical or different.

Production of the Multispecific Antibodies

The skilled person may refer to international patent application WO2013/005194, herein incorporated by reference, for general techniques of expressing multispecific antibodies.

Also, herein described is a polynucleotide comprising a sequence encoding a protein chain of the molecule or antibody of the invention. Said polynucleotide may also comprise additional sequences: in particular it may advantageously comprise a sequence encoding a leader sequence or signal peptide allowing secretion of said protein chain. Host cells transformed with said polynucleotide are also disclosed.

Typically, the amino acid sequences of different monoclonal antibodies are used to design the DNA sequences, optionally after codon optimization for mammalian expression. For the heavy chain, the DNAs encoding signal peptides, variable region and constant CH1 domain of Fab1 followed the hinge linker and variable region and constant CH1 domain of Fab2 with flanking sequences for restriction enzyme digestion are synthesized. For the light chain, the DNAs encoding signal peptides and variable and constant Kappa regions are synthesized.

Nucleic acids encoding heavy and light chains of the antibodies of the invention are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

In one example, both the heavy and light chain-coding sequences (e.g., sequences encoding a VH and a VL, a VH-CH1 and a VL-CL, or a full-length heavy chain and a full-length light chain) are included in one expression vector. In another example, each of the heavy and light chains of the antibody is cloned into an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that or those encoding the light chains can be introduced into different host cells for expression each of the heavy and light chains, which can then be purified and assembled to form intact antibodies in vitro.

In a particular embodiment, a host cell is co-transfected with three independent expression vectors, such as plasmids, leading to the coproduction of all three chains (namely the heavy chain HC, and two light chains LC1 and LC2, respectively) and to the secretion of the multispecific, e.g. bispecific, antibody.

More especially the three vectors may be advantageously used in a following molecular ratio of 2:1:1 (HC:LC1:LC2).

The host cell transfected with an expression vector comprising the polynucleotide that encodes a heavy chain as defined herein, may further be transformed with at least two polynucleotides encoding two different light chains: a first light chain, which pairs specifically with a first VH/CH1 region of said heavy chain; a second light chain, which pairs specifically with a second VH/CH1 region of said heavy chain.

In a further embodiment, the host cell may be additionally transformed with a polynucleotide encoding a third light chain, which is different from the first and second light chains, and which pairs specifically with a third VH/CH1 region of said heavy chain.

The recombinant vectors for expression the antibodies described herein typically contain a nucleic acid encoding the antibody amino acid sequences operably linked to a promoter, either constitutive or inducible. The vectors can be suitable for replication and integration in prokaryotes, eukaryotes, or both. Typical vectors contain transcription and translation terminators, initiation sequences, and promoters useful for regulation of the expression of the nucleic acid encoding the antibody. The vectors optionally contain generic expression cassettes containing at least one independent terminator sequence, sequences permitting replication of the cassette in both eukaryotes and prokaryotes, i.e., shuttle vectors, and selection markers for both prokaryotic and eukaryotic systems.

Multispecific, e.g. bispecific, antibodies as described herein may be produced in prokaryotic or eukaryotic expression systems, such as bacteria, yeast, filamentous fungi, plant insect (e.g. using a baculovirus vector), and mammalian cells. It is not necessary that the recombinant antibodies of the invention are glycosylated or expressed in eukaryotic cells; however, expression in mammalian cells is generally preferred. Examples of useful mammalian host cell lines are human embryonic kidney line (293 cells), baby hamster kidney cells (BHK cells), Chinese hamster ovary cells/− or +DHFR (CHO, CHO-S, CHO-DG44, Flp-in CHO cells), African green monkey kidney cells (VERO cells), and human liver cells (Hep G2 cells).

Mammalian tissue cell culture is preferred to express and produce the polypeptides because a number of suitable host cell lines capable of secreting intact immunoglobulins have been developed in the art, and include the CHO cell lines, various Cos cell lines, HeLa cells, preferably myeloma cell lines (such as NS0), or transformed B-cells or hybridomas.

In a most preferred embodiment, the multispecific, e.g. bispecific, antibodies of the invention are produced by using a CHO cell line, most advantageously a CHO-S or CHO-DG-44 cell lines or their derivatives.

Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium phosphate treatment or electroporation may be used for other cellular hosts. (See generally Sambrook et al., Molecular Cloning: A Laboratory Manual (Cold Spring Harbor Press, 2nd ed., 1989). When heavy and light chains are cloned on separate expression vectors, the vectors are co-transfected to obtain expression and assembly of intact immunoglobulins. Host cells are transformed or transfected with the vectors (for example, by chemical transfection or electroporation methods) and cultured in conventional nutrient media (or modified as appropriate) for inducing promoters, selecting transformants, or amplifying the genes encoding the desired sequences.

The expression of the antibodies may be transient or stable.

Preferably, the multispecific, e.g. bispecific, antibodies are produced by the methods of stable expression, in which cell lines stably transfected with the DNA encoding all polypeptide chains of a multispecific, e.g. bispecific antibody, such as BiXAb-6567, are capable of sustained expression, which enables manufacturing of therapeutics. For instance, stable expression in a CHO cell line is particularly advantageous.

Once expressed, the whole antibodies, their dimers, individual light and heavy chains, or other immunoglobulin forms of the present invention can be further isolated or purified to obtain preparations that substantially homogeneous for further assays and applications. Standard protein purification methods known in the art can be used. For example, suitable purification procedures may include fractionation on immunoaffinity or ion-exchange columns, ethanol precipitation, high-performance liquid chromatography (HPLC), sodium dodecyl sulfate polyacrylamide gel electrophoresis (SDS-PAGE), ammonium sulfate precipitation, and gel filtration (see generally Scopes, Protein Purification (Springer-Verlag, N.Y., 1982). Substantially pure immunoglobulins of at least about 90 to 95% homogeneity are preferred, and 98 to 99% or more homogeneity most preferred, for pharmaceutical uses.

In vitro production allows scale-up to give large amounts of the desired multispecific, e.g. bispecific, antibodies of the invention. Such methods may employ homogeneous suspension culture, e.g. in an airlift reactor or in a continuous stirrer reactor, or immobilized or entrapped cell culture, e.g. in hollow fibers, microcapsules, on agarose microbeads or ceramic cartridges.

Applications

The protein constructs or multispecific antibodies of the invention can be used in all the applications of multispecific antibodies. In particular they can be used to obtain medicaments useful in a broad range of therapeutic applications and diagnostic medicinal applications in patients (conjugated to radioactive, fluorescent, chemiluminescent, or any other labels), or in vitro, (e.g. for cell and tissue staining employing immunohistochemistry, immunoblot, and immunofluorescence techniques). These medicinal or diagnostic products are also part of the object of the invention.

A further aspect of the invention is a pharmaceutical composition comprising a protein construct or an antibody according to the invention. Another aspect of the invention is the use of a protein construct or an antibody according to the invention for the manufacture of a pharmaceutical composition. A further aspect of the invention is a method for the manufacture of a pharmaceutical composition comprising a protein construct or an antibody according to the invention.

In another aspect, the present invention provides a composition, e.g. a pharmaceutical composition, containing a protein construct or an antibody as defined herein, formulated together with a pharmaceutical carrier.

A composition of the present invention can be administered by a variety of methods known in the art.

The following examples are provided by way of illustration and are not intended to be limiting the instant invention.

EXAMPLES

Example 1. Preparation of Bispecific Antibody of the Invention BiXAb-6567

Gene Synthesis

The amino acid sequences of anti-CD38 (daratumumab) and anti-PDL1 (atezolizumab) were used to design the DNA sequences, after codon optimization for mammalian expression, using the GeneScript program. These antibodies are referred to as the "parental" anti-CD38 and the "parental" anti-PD-L1 mAbs.

The DNA construct of the heavy chain was designed as such: signal peptide, followed by sequence SEQ ID NO:7 [consisting of the variable region, followed by the constant CH1 domain of Fab1 (anti-CD38), in which mutations Leu to Gln and Ser to Val at Kabat positions 124 and 188 were introduced, respectively, followed by the linker, followed by the variable region, followed by the constant CH1 domain of Fab2 (anti-PD-L1), in which mutation Thr to Asp at Kabat position 192 was introduced]; flanking sequences for restriction enzyme digestion were introduced on both ends of the heavy chain DNA construct. The DNA construct for the light chain was designed as such: signal peptide (SEQ ID NO:21), followed by the variable region, followed by the constant Kappa region. For the anti-CD38 light chain (SEQ ID NO:15), mutations where introduced at Kabat positions 133 (Val to Thr) and 176 (Ser to Val) in the constant Kappa domain. For the anti-PDL1 light chain (SEQ ID NO:18), mutations at Kabat positions 114 (Ser to Ala) and 137 (Asn to Lys) were introduced into the constant Kappa domain. All DNA constructs were synthesized by Gene Art.

PCR reactions, using PfuTurbo Hot Start, were carried out to amplify the inserts, which were then digested with NotI and ApaI, and NotI and HindIII for heavy and light chains, respectively. The double digested heavy chain fragments were ligated with NotI and ApaI treated pcDNA3.1 expression vector (Invitrogen) into which the human IgG1 hinge followed by the CH2-CH3 domains were already inserted. The double-digested light chain fragments were ligated with NotI and HindIII treated pcDNA3.1 expression vector (Invitrogen). Plasmid DNAs were verified by double strand DNA sequencing.

Expression and Purification

The bispecific antibody BiXAb-6567 was produced employing transient gene expression by co-transfecting 3 genes coded on separate vectors in a 2:1:1=HC:LC1:LC2 molecular ratio (1 continuous heavy chain (HC) and 2 light chains (LC)) in CHO-S cells adapted to serum-free medium in suspension (CHO SFM-II medium, LIFE TECHNOLOGIES). Typically, for 50 mL scale expression, a total of 50 μg of plasmid DNA (25 μg heavy chain, 12.5 μg of anti-CD38 light chain and 12.5 μg of anti-PD-L1 light chain) were mixed in a 1.5 mL Eppendorf tube, then 1 mL of CHO SFM medium containing 25 μL of 3 mg/mL PEI transfection reagent pH7.0 (Polyplus) was added, and the reaction incubated at room temperature for 20 min. The DNA-PEI mixture was subsequently added to 49 mL of Life Technologies' Invitrogen FreeStyle™ CHO-S cells at 1~2×106/mL in a 125 mL shake flask. Cells were shaken for 6 days. The supernatant was harvested by centrifugation at 3,000 rpm for 15 min. The expression titer of BiXAb-6567 in the supernatant was determined using ForteBio's protein A biosensors (OCTET Systems). BiXAb-6567 was then purified on protein A affinity resin (MABSELECT SURE, GE Healthcare Life Sciences). The antibody was eluted from protein A using 0.1 M glycine pH 3.5, and the eluate was neutralized by 1 M TRIS. The purified antibody, in Dulbecco's PBS (Lonza), was sterile-filtered (0.2 μM sterile filters, Techno Plastic Products AG), and the final concentration determined by reading the optical density (OD) at 280 nm (EPPENDORF BIO SPECTROMETER).

BiXAab-6567 typically exhibited good expression titer (>180 mg/liter) in transient CHO expression. This level of expression is comparable to the level of expression seen with conventional monoclonal antibodies.

SDS Polyacrylamide Gel Electrophoresis

Figure 1:
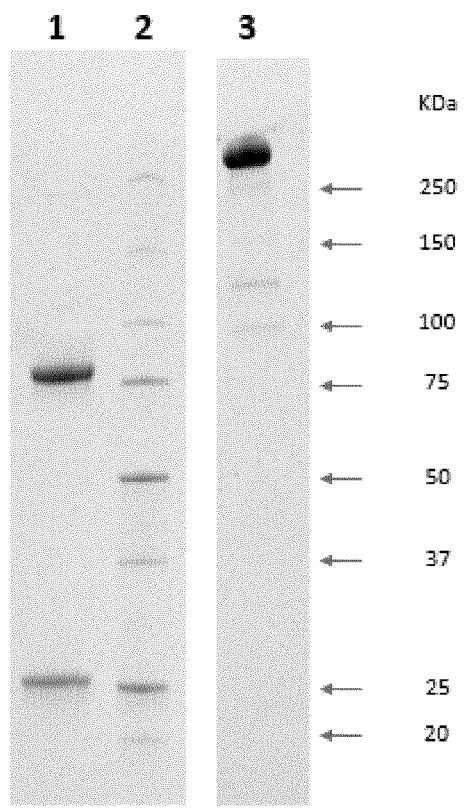
FIG. 1 shows the SDS polyacrylamide gel electrophoresis of BiXAb-6567 under reducing and non-reducing conditions. Lane 1: the migration of BiXAb-6567 under reducing conditions; lane 2: molecular weight markers with the weight of each band indicated; lane 3: the migration of BiXAb-6567 under non-reducing conditions.

In order to evaluate the quality of purified BiXAb-6567, we performed SDS-PAGE (Experion™ automated electrophoresis system, BioRad). In the presence of sodium dodecyl sulfate (SDS) in the running buffer, the rate at which an antibody migrates in the gel depends primarily on its size, enabling molecular weight determination. This assay was performed under non-reducing conditions and under reducing conditions; the latter permits disruption of the disulfide bonds, and hence visualization of individual polypeptide chains (the light chains and the heavy chain). The SDS-PAGE data are presented in FIG. 1. Under non-reducing conditions, the quaternary structure of the antibody is maintained, and the molecular weight observed should represent the sum of the molecular weights of the different heavy and light chains. The bispecific antibody of the invention (BiXAb-6567) consists of six chains: two heavy chains and four light chains. The theoretical molecular weight of BiXAb-6567 is 244.40 kDa, not accounting for post-translational modifications (PTM), e.g. N-glycosylation in the Fc at asparagine 297. The gel was calibrated using a mixture of standards of known molecular weight. The non-reducing data exhibit a major band running close to the 250 kDa molecular weight standard, which is in accordance with the calculated molecular weight and the expected glycosylation of two asparagines at position 297 in the Fc domain. Under reducing conditions, dithiothreitol (DTT) further denatures BiXAb-6567 by reducing the disulfide linkages and breaking the quaternary structure, and thus the six polypeptide chains should migrate separately in the gel according to their molecular weight. The two identical heavy chains of BiXAb-6567 co-migrate as a single band, and the two pairs of light chains, due to their nearly identical molecular weight, co-migrated as the second band. Therefore, the data exhibit two major bands, at approximately 75 kDa and 25 kDa, based on the mobility of the molecular weight standards. Each heavy chain possessed one N-glycosylation site at asparagine 297, which explains the broadness of the higher molecular weight band and the observed molecular weight slightly higher than calculated (75.44 kDa); this broadening is typical for glycosylated proteins. The calculated molecular weights of the light chains of anti-CD38 (23.40 kDa) and anti-PD-L1 (23.36 kDa) are very similar, and thus resulted in their co-migration.

In conclusion, the SDS-PAGE of BiXAb-6567 exhibited the expected profiles, under both non-reducing and reducing conditions, and was in agreement with the calculated theoretical molecular weights, when accounting for the existence of an N-glycosylation site in the heavy chain.

Size Exclusion Chromatography Analysis

Protein aggregation is frequently observed in engineered protein molecules. We performed analytical size exclusion chromatography (SEC) to assay the high molecular weight species content of the single-step affinity-purified BiXAb-6567 preparation (see Expression and Purification of variants). We employed an SEC-s3000 (300×7.8 mm) column (BioSep) and an Aktapurifier 10 system (GE Healthcare); the assay was conducted at a flow rate of 1 mL/min using PBS buffer pH 7.4.

Figure 2:
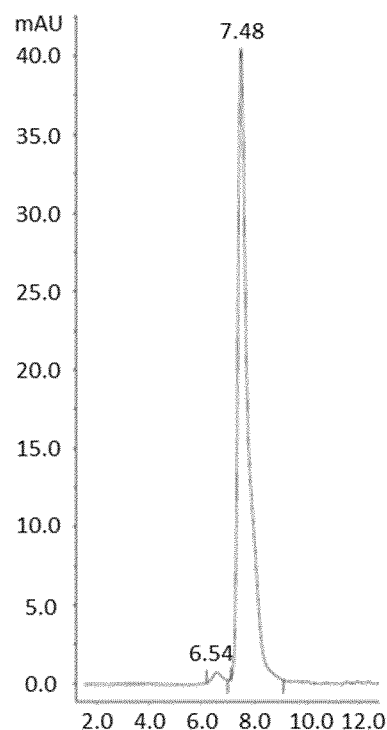
FIG. 2 shows the Size Exclusion chromatography analysis of BiXAb-6567.

The SEC chromatogram presented in FIG. 2 demonstrated that the main peak corresponded to the expected size of the monomeric BiXAb-6567; this peak represented 98.2% of the total sample. In addition, a small peak corresponding to higher molecular weight species (possibly dimers) was observed; this peak represented 1.8% of the total sample. Thus, we concluded that the percentage content of higher molecular weight species is minor, and is similar to conventional monoclonal antibodies produced in CHO expression systems. The narrow and symmetric shape of the monomeric peak suggested that BiXAb-6567 was correctly assembled and was represented by a single species.

Example 2. Characterization of BiXAb-6567 by Differential Scanning Calorimetry (DSC)

Differential Scanning Calorimetry (DSC) was used to compare the thermal stability of BiXAb-6567, the parental anti-CD38 mAb, and the parental anti-PD-L1 mAb. A Microcal™ VP-Capillary DSC system (Malvern Instruments) was used to perform differential scanning calorimetry experiments.

All samples were centrifuged (20,000×g, 5 min, 4° C.), and their protein content was quantitated prior to the DSC analysis using a Nanodrop ND-1000 spectrophotometer (Thermo Scientific) employing the IgG analysis program. For assay, all samples were diluted in PBS to a final concentration of 1 mg/mL.

The pre-equilibration time was 3 min, and the resulting thermograms were acquired between 20 and 110° C. at a scan rate of 60° C./h, a filtering period of 25 sec, and medium feedback. Prior to sample analysis, 5 buffer/buffer scans were measured to stabilize the instrument, and a buffer/buffer scan was performed between each protein/buffer scan. The data were fit to a non-2-state unfolding model, with the pre- and post-transition adjusted by subtraction of the baseline.

Figure 3:
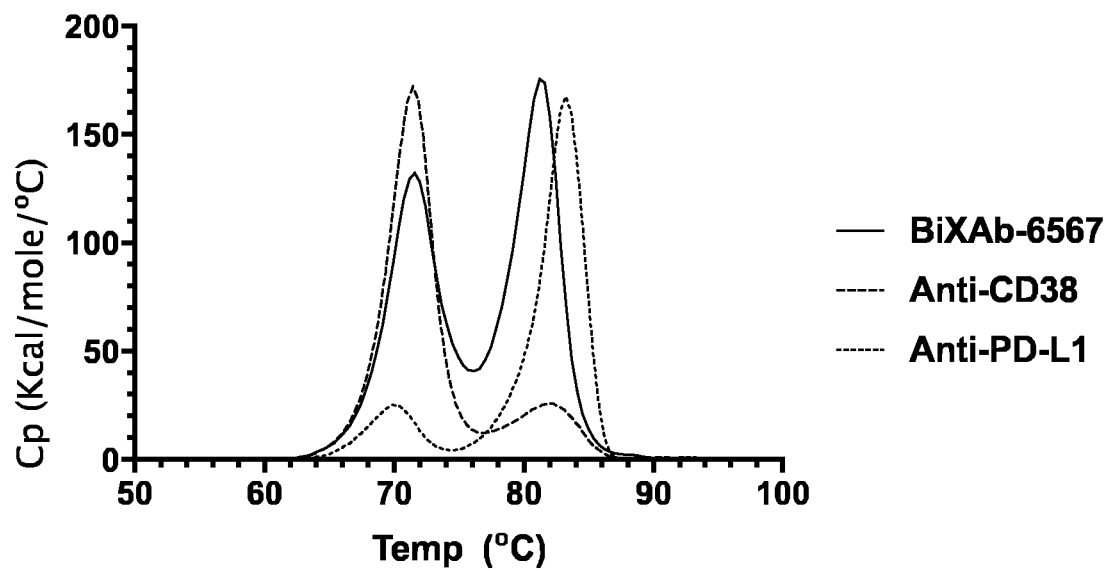
FIG. 3 shows the melting profiles of the two parental antibodies (anti-CD38 and anti-PD-L1) and BiXAb-6567 as determined by Differential Scanning Calorimetry.

The DSC curves presented in FIG. 3 (covering the 50 to 100° C. range) demonstrated the manner in which individual Fv regions can lead to different Fab unfolding profiles; this experiment also demonstrated that the Fv regions dictate the apparent stabilities of the Fabs. The DSC profile of the anti-CD38 mAb exhibited two transitions: a large peak having a Cp max of 170 Kcal/mole/° C. and a Tm1 of 70.9° C., corresponding to the unfolding of both CH2 and Fab domains, and a small peak having a Cp max of 20 Kcal/mole/° C. and a Tm2 of 81.5° C., corresponding to the unfolding of the CH3 domain. The DSC profile of the anti-PD-L1 mAb exhibited two transitions: a small peak having a Cp max of 20 Kcal/mole/° C. and a Tm1 of 69.9° C., corresponding to the unfolding of the CH2 domain, and a large peak having a Cp max of 160 Kcal/mole/° C. and a Tm2 of 83.4° C., corresponding to the unfolding of both CH3 and Fab domains.

The DSC profile of BiXAb-6567 also exhibited two transitions with two large peaks. The first peak had a Cp max of 130 Kcal/mole/° C. and a Tm1 of 71.5° C., and corresponded to the unfolding of the CH2 and Fab domains of the anti-CD38 mAb; the second peak had a Cp max of 170 Kcal/mole/° C. and a Tm2 of 81.5° C., and corresponded to the unfolding of the CH3 and Fab domains of the anti-PD-L1 mAb. Thus, the DSC profile of BiXAb-6567 resembled the superposition of the two DSC profiles of the two parental mAbs, and illustrated the excellent assembly and stability of BiXAb-6567. The Tonset of BiXAb-6567 (63.3° C.) was similar to that of the parental mAbs (anti-CD38 Tonset=63.5° C. and anti-PD-L1 Tonset=63.2° C.), indicating that BiXAb-6567 possessed stability properties similar to those of the parental antibodies. The calculated ΔH of BiXAb-6567 was 1560 kcal/mole, reflecting the larger size of the bispecific molecule relative to the two parental antibodies (anti-CD38 ΔH=963 kcal/mole and anti-PD-L1 ΔH=820 kcal/mole).

Definitions

Tm or denaturation/melting temperature is the point at which the concentration of the unfolded and folded species is equal, and is the midpoint of the unfolding transition. As a parameter, it describes the susceptibility of the protein to thermal denaturation, and thus it relates to the stability of the protein. The higher the Tm the more stable the protein.

Tonset is the temperature at which the unfolding transition begins. The values for this parameter are usually 5 to 10° C. lower than the Tm. It is also a parameter describing protein stability, but with relevance to the resistance to thermal denaturation.

ΔH is the calorimetric enthalpy of unfolding, and reflects the disruption of intramolecular interactions in the protein (i.e. breaking of intra- and inter-domain interactions). The thermal unfolding process is endothermic, and thus yields positive enthalpy values. The calorimetric enthalpy (ΔH) is the area under the thermal unfolding transition peak.

Example 3. Cell Free Binding Properties of BiXAb-6567

Direct CD38 Antigen-Binding Plate ELISA Assay

100 µl of either parental mAb, anti-CD38 or anti-PDL1, each at a concentration of 3 µg/mL, prepared by dilution with PBS pH 7.4, were used to coat MAXISORP plates at 4° C. overnight. Also, BiXAb-6567, at a concentration of 5 µg/mL, prepared by dilution with PBS pH 7.4, was used to coat MAXISORP plates at 4° C. overnight. The plates were washed 5 times with 1×PBS containing 0.05% TWEEN-20 (PBST), and then blocked with 200 µL/well 1% BSA in 1×PBS at room temperature for 2 hrs. The plates were subsequently washed 5 times with 1×PBST. A seven-point 3-fold dilution series of recombinant CD38 His/Flag-tagged (Creative Biomart) in 1×PBS, starting at 1 µg/mL, was prepared; 100 µL of each dilution step was added per assay well. The plates were incubated at room temperature for 1 hr, and washed 5 times with 1×PBST. 100 µL/well of anti-Flag-tag antibody-conjugated HRP (Abcam), diluted 10,000-fold in 1×PBS, was added and the plates were incubated at room temperature for 1 hr. After 5 washes with 1×PBST, 100 µL/well of TMB substrate in 1×PBS was added for colorimetric readout, and the plates incubated for 15 min at room temperature for color development. The assay data were collected employing a VICTOR2 microplate reader (Perkin Elmer) at 650 nm.

BiXAb-6567 exhibited a dose-dependent binding curve very similar to that of the parental anti-CD38 antibody (FIG. 4A). The EC50 of CD38 binding for both antibodies were as follows: EC50[BiXAb-6567]=171 ng/mL and EC50[anti-CD38]=199 ng/mL. This result suggested that BiXAb-6567 possessed correctly assembled anti-CD38 Fab domains, since it exhibited binding similar to that of the parental anti-CD38 mAb. The parental anti-PDL1 mAb, used as a negative control, did not exhibit any binding, as expected.

Direct PDL1 Antigen-Binding Plate ELISA Assay

100 µL of biotinylated human PD-L1 protein (AcroBiosystems) at a concentration of 1 µg/mL, prepared by dilution with 1×PBS pH7.4, was used to coat MAXISORP plates at 4° C. overnight. The plates were washed 5 times with PBST, and then blocked with 200 µL/well 1% BSA in 1×PBS at room temperature for 2 hrs. The plates were subsequently washed 5 times with 1×PBST. Seven-point 3-fold dilution series of either the anti-CD38 mAb (starting at 0.3 mg/mL), or the anti-PD-L1 mAb (starting at 0.3 mg/mL), or BiXAb-6567 (starting at 0.5 mg/mL) in 1×PBS were prepared; 100 µL of each dilution step was added per assay well. The plates were incubated at room temperature for 1 hr and washed 5 times with 1×PB ST. 100 µL/well of anti-human antibody (IgG H&L)-conjugated HRP (Abliance), diluted 5,000-fold in 1×PBS, was added, and the plates were incubated at room temperature for 1 hr. After 5 washes with 1×PBST, 100 µL/well of TMB substrate in 1×PBS was added for colorimetric readout, and the plates incubated for 15 min at room temperature for color development. The assay data were collected employing a VICTOR2 microplate reader (Perkin Elmer) at 650 nm.

BiXAb-6567 exhibited a dose-dependent binding curve very similar to that of the parental anti-PD-L1 antibody (FIG. 4B). The EC50 of PD-L1 binding for both antibodies were as follows: EC50[BiXAb-6567]=93 ng/mL and EC50 [anti-PD-L1]=72 ng/mL. This result suggested that BiXAb-6567 possessed correctly assembled anti-PD-L1 Fab domains, since it exhibited binding similar to that of the parental anti-PD-L1 mAb. The parental anti-CD38 mAb, used as a negative control, did not exhibit any binding, as expected.

Dual Antigen-Binding ELISA Assay

100 µL of recombinant human Fc-tagged CD38 (Creative BioMart), at 2 µg/mL prepared by dilution with 1×PBS pH7.4, was used to coat MAXISORP plates at 4° C. overnight. The plates were washed 5 times with 1×PBST, and then blocked with 200 µL/well 1% BSA in 1×PBS at room temperature for 2 hrs. The plates were washed 5 times with 1×PBST. A seven-point three-fold dilution series in 1×PBS of BiXAb-6567 (starting at 1 µg/mL) was prepared, and 100 µL of each dilution step was added per assay well. The plates were incubated at room temperature for 1 hr, and subsequently washed 5 times with 1×PBST. 100 µL/well of 1 µg/mL biotinylated human PD-L1 (AcroBiosystems) in 1×PBS was added, and the plates were incubated at room temperature for 1 hr. After 5 washes with 1×PBST, 100 µL/well of 0.1 µg/mL of streptavidin-conjugated HRP (Biotechne) prepared by dilution with 1×PBS was added. The plates were incubated at room temperature for 1 hr. After 5 washes with 1×PBST, 100 µL/well of TMB substrate in 1×PBS was added for colorimetric readout, and the plates incubated for 15 min at room temperature for color development. The assay data were collected employing a VICTOR2 microplate reader (Perkin Elmer) at 650 nm.

BiXAb-6567 exhibited a dose-dependent binding curve in the dual ELISA format, suggesting that it possessed correctly assembled anti-CD38 and anti-PD-L1 Fab domains (FIG. 4C). This demonstrated that BiXAb-6567 is a bispecific antibody capable of binding CD38 and PD-L1 simultaneously with EC50=144 ng/mL. Neither of the two parental mAbs, anti-CD38 or anti-PDL1, exhibited any binding in this dual ELISA format, as expected.

Example 4. Determination of Relative Binding Activity by Fluorescence-Activated Cell Sorting (FACS)

CHO-CD38 cells (CHO cells stably transfected with full length human CD38) were cultured in DMEM-Glutamax-I medium supplemented with 100 µg/ml penicillin, 100 µg/ml streptomycin, 10% fetal calf serum and 500 µg/ml geneticin. SKOV-3 cells and RPMI-8226 cells were cultured in RPMI 1640-Glutamax-I medium, supplemented with 100 µg/ml penicillin, 100 µg/ml streptomycin, and 10% fetal calf serum.

3×105 cells (CHO-CD38, or SKOV-3, or RPMI-8226) per each sample were used. Cells were washed 1× with the PBA solution (PBS supplemented with 1% BSA and 0.05% Na-azide). For the determination of the FACS profiles, the cells were stained with the respective antibodies at a concentration of 50 µg/ml in a volume of 30 µl. For the titration of BiXAb-6567 and the parental anti-CD38 antibody, and subsequent determination of the binding parameters, CHO-CD38 cells were stained with the respective antibodies at the indicated concentrations in a volume of 30 µl. Cells were incubated for 30 min on ice and then washed 2 times with 1 ml of PBA solution. Cells were incubated with fluorescently labeled anti-human kappa or anti-human IgG Fc gamma specific secondary antibodies on ice in the dark for 30 min, and then washed 2 times with 1 ml PBA solution; lastly, cells were re-suspended in a final volume of 500 µl PBA solution. Samples were assayed using either an Epics-XL or a Navios flow cytometer (Beckman Coulter). 10.000 events were acquired in each experiment.

The binding profiles of BiXAb-6567 and the parental anti-CD38 and anti-PD-L1 parental antibodies are presented in FIGS. 5A-C. We chose to test a multiple myeloma cell line, RPMI-8226, which expresses high levels of CD38 and negligible levels of PD-L1 (FIG. 5A); a CHO-CD38 cell line that expressed a very high level of CD38 due to stably transfected full length CD38 (FIG. 5B); and an ovarian cancer cell line SKOV-3, which is known to express PD-L1 (FIG. 5C). These profiles exhibited a single peak for BiXAb-6567 that was very similar to the profiles of both parental antibodies on the 3 cell lines. This suggested that BiXAb-6567 is correctly folded and possesses binding attributes similar to those of the parental antibodies. As expected, CHO-CD38 expressed only CD38 and no PD-L1, whereas SKOV-3 expressed only PD-L1 and no CD38.

In order to quantitatively confirm that the binding properties of BiXAb-6567 are similar to those of the parental anti-CD38 antibody, a titration of BiXAb-6567 and the anti-CD38 parental antibody was performed employing CHO-CD38 cells, as presented in FIG. 6. The EC50 of BiXAb-6567 was determined to be 17.1 nM and that of the parental anti-CD38 was 8.5 nM, confirming the similar binding properties of the anti-CD38 Fab domains in BiXAb-6567 and in the parental anti-CD38 antibody. Negative controls in this experiment, anti-PD-L1 and anti-CD20 antibodies, demonstrated no binding to CHO-CD38 cells, as expected.

Example 5. Antibody Dependent Cell-Mediated Cytotoxicity (ADCC) with Unfractionated Non-Preactivated Mononuclear Cells (MNC)

CHO-CD38, SKOV-3, and RPMI-8226 cells were cultured as described in Example 4 above.

For preparation of MNC the following procedure was employed. Freshly drawn peripheral blood was anti-coagulated with citrate. Subsequently, 5 ml of FICOLL-PAQUE PLUS solution was layered with 6 ml anti-coagulated whole blood. Samples were centrifuged for 20 min at 2,500 rpm at RT with no subsequent centrifuge breaking. MNC were collected from the plasma/Ficoll interface. The MNC cell suspension was diluted 1:10 in PBS and centrifuged for 5 minutes at 1,800 rpm at room temperature. The supernatant was removed, and the erythrocytes were lysed by addition of 45 ml ice-cold distilled water to the cell suspension for 30 seconds, after which 5 ml of 10×PBS was added. The cells were centrifuged for 5 min at 1800 rpm at room temperature and washed with 1×PBS three times to remove platelets. Finally, cells were re-suspend in 5 ml cell culture medium. Cell numbers were adjusted to achieve 40:1=Effector cell: Tumor cell ratio in the ADCC assays.

For the ADCC $^{51}$Chromium release assay, $1\times10^6$ target cells (RPMI 8226, SKOV-3, or CHO-CD38) were incubated with 100 µCi 51Chromium in 200 µl PBS for 2 hours at 37° C. and 5% CO2. After 2 hours incubation, cells were washed three times with 7 ml of medium and finally re-suspended at a concentration of 0.1×106 cells/ml. Target cells (5,000 cells/well) and MNC in the presence of antibodies were incubated in a 96-well micro-titer plate (200 µl assay volume) for 3 hours at 37° C. and 5% CO2. For the determination of maximal target cell lysis (=maximal cpm) TRI-TON X-100 was added. To determine basal $^{51}$Chromium release (=basal cpm) target cells were not further manipulated. After 4 hr incubation, micro-titer plates were centrifuged for 5 min at 2000 rpm and 25 µl supernatant was mixed with 125 µl of OPTIPHASE Supermix (Perkin Elmer) and incubated in a shake incubator for 1 min. Samples were assayed in a MICROBETA TriLux (Perkin Elmer) beta-counter instrument. Target cell lysis was calculated using the following formula:

$$\% \text{ lysis} = (\text{experimental cpm} - \text{basal cpm})/(\text{maximal cpm} - \text{basal cpm}) \times 100.$$

All of the measurements were performed in triplicate.

ADCC assays of CD38+ cells (RPMI-8226 and CHO-CD38) were performed employing non-pre-activated MNC as effector cells (FIGS. 7 and 8) The assays showed potent cytotoxicity of BiXAb-6567 and the anti-CD38 antibody on RPMI-8226 cells with EC50 of 0.8 nM and 0.3 nM, respectively; on CHO-CD38 cells, the cytotoxicity of BiXAb-6567 and the anti-CD38 antibody had EC50 of 0.2 nM and 0.07 nM, respectively. Anti-PD-L1 showed minimal activity on both cells lines; two negative control mAbs, anti-CD20 and anti-HER2, did not facilitate any lysis, as expected. These results demonstrate the potent ADCC activity of BMX-6567 against CD38+ cells, which is similar to that of the parental anti-CD38 antibody.

Example 6. ADCC with Enriched Pre-Activated NK Cells

SKOV3 cells, RPMI 8226, and CHO-CD38 cells were cultured as described in Example 4. MNC were prepared as described in Example 5. NK cells were isolated from MNC by negative selection employing the "NK cell isolation kit, human" (Miltenyi) according to the manufacturer's instructions. NK cells were cultivated over night at a seeding density of $2\times10^6$ cells/ml in RPMI medium supplemented with 10% fetal calf serum. IL-12 or IL-15 was added to a final concentration of 10 ng/ml. ADCC assays were performed as outlined in Example 5 with the exception that the Effector cell:Tumor cell ratio was kept at 10:1 and the duration of the reaction was reduced to 3 hr.

The ADCC properties of the anti-PD-L1 moiety of the BiXAb-6567 were assayed on the PD-L1+ cell line SKOV-3 employing either IL-12 or IL-15 pre-activated enriched NK cells. The results are presented in FIGS. 9 and 10. This experiment compared the ADCC properties of BiXAb-6567 with those of the parental anti-PD-L1 antibody; as a positive control an anti-HER2 antibody was employed, and as negative controls an anti-CD20 antibody and the parental anti-CD38 antibody were employed since SKOV-3 cells are PD-L1+/HER2+/CD20−/CD38−. FIGS. 9 and 10 demonstrate the potent ADCC activity of BiXAb-6567 and the parental anti-PD-L1 antibodies, independently of whether IL-12 or IL-15 was employed in culturing the NK cells. The EC50 of BiXAb-6567 and the parental anti-PD-L1 antibodies were 0.007 nM and 0.03 nM, respectively, when IL-12 was used. The profiles were even more similar when IL-15 was employed; however the curve fits did not converge, thus preventing the calculation of EC50 values. These results demonstrate the potent ADCC activity of BMX-6567 against PD-L1+ cells, which is similar to that of the parental anti-PD-L1 antibody.

The invention claimed is:

1. A protein construct comprising a mutated Fab fragment which is:
 a) a Fab fragment consisting of:
  VH and VL domains of an antibody of interest;
  a CH1 domain which is derived from the CH1 domain of an immunoglobulin by substitution of the threonine residue at position 192 of said CH1 domain with an aspartic acid; and
  a CL domain which is derived from the CL domain of an immunoglobulin by substitution of the asparagine residue at position 137 of said CL domain with a lysine residue and substitution of the serine residue at position 114 of said CL domain with an alanine residue; or
 b) a Fab fragment consisting of:
  VH and VL domains of an antibody of interest;
  a CH1 domain which is derived from the CH1 domain of an immunoglobulin by substitution of the leucine residue at position 124 of said CH1 domain with a glutamine and substitution of the serine residue at position 188 of said CH1 domain with a valine residue; and
  a CL domain which is derived from the CL domain of an immunoglobulin by substitution of the valine residue at position 133 of said CL domain with a threonine residue and substitution of the serine residue at position 176 of said CL domain with a valine residue,
 wherein the sequence position numbers used herein for the CH1 and CL domains refer to Kabat numbering.

2. The protein construct of claim 1, that comprises a multispecific antigen-binding fragment comprising at least two Fab fragments with different CH1 and CL domains, wherein each Fab fragment recognizes a different epitope of interest, and said Fab fragments are tandemly arranged in any order, the C-terminal end of the CH1 domain of a first Fab fragment being linked to the N-terminal end of the VH domain of the following Fab fragment through a polypeptide linker,
 wherein at least one Fab fragment consists of:
  a) a Fab fragment consisting of:
   VH and VL domains of an antibody of interest;
   a CH1 domain which is derived from the CH1 domain of an immunoglobulin by substitution of the threonine residue at position 192 of said CH1 domain with an aspartic acid; and
   a CL domain which is derived from the CL domain of an immunoglobulin by substitution of the asparagine residue at position 137 of said CL domain with a lysine residue and substitution of the serine residue at position 114 of said CL domain with an alanine residue; or
  b) a Fab fragment consisting of:
   VH and VL domains of an antibody of interest;
   a CH1 domain which is derived from the CH1 domain of an immunoglobulin by substitution of the leucine residue at position 124 of said CH1 domain with a glutamine and substitution of the serine residue at position 188 of said CH1 domain with a valine residue; and
   a CL domain which is derived from the CL domain of an immunoglobulin by substitution of the valine residue at position 133 of said CL domain with a threonine residue and substitution of the serine residue at position 176 of said CL domain with a valine residue,
  wherein the sequence position numbers used herein for the CH1 and CL domains refer to Kabat numbering.

3. The protein construct of claim 2, said protein construct being a multispecific antibody having two identical antigen-binding arms, each consisting of a multispecific antigen-binding fragment.

4. The protein construct of claim 3, which has an immunoglobulin-like structure, comprising:
 two identical antigen-binding arms each consisting of a multispecific antigen-binding fragment;
 the dimerized CH2 and CH3 domains of an immunoglobulin; and
 the hinge region of an IgA, IgG, or IgD, linking the C-terminal ends of CH1 domains of the antigen-binding arms to the N-terminal ends of the CH2 domains.

5. The protein construct of claim 4, which comprises at least two heavy chains and four light chains,
 wherein each heavy chain comprises:
 a) Fc region of an immunoglobulin comprising Hinge-CH2-CH3 domains,
 b) which Fc region is linked to Fab heavy chain CH1-VH of antibody 1 (Ab1) by said Hinge domain,
 c) which in turn is linked to Fab heavy chain CH1-VH of antibody 2 (Ab2) by a polypeptide linker sequence, and the polypeptide linker sequence links the N-terminus of said Fab heavy chain VH domain of Ab1 with the C-terminus of said CH1 domain of Ab2,
 and the four light chains comprise Fab light chains CL-VL of Ab1 and Fab light chains CL-VL of Ab2 associated with their cognate heavy chain domains;
 wherein Ab1 and Ab2 recognize different epitopes,
 and wherein the Fab CH1 domain of one of Ab1 or Ab2 is a mutated domain that derives from the CH1 domain of an immunoglobulin by substitution of the threonine residue at position 192 of said CH1 domain with an aspartic acid and the cognate CL domain is a mutated domain that derives from the CL domain of an immunoglobulin by substitution of the asparagine residue at position 137 of said CL domain with a lysine residue and substitution of the serine residue at position 114 of said CL domain with an alanine residue, and/or wherein the Fab CH1 domain of one or the other of Ab1 or Ab2 is a mutated domain that derives from the CH1 domain of an immunoglobulin by substitution of the leucine residue at position 124 of said CH1 domain with a glutamine and substitution of the serine residue at position 188 of said CH1 domain with a valine residue, and the cognate CL domain is a mutated domain that derives from the CL domain of an immunoglobulin by substitution of the valine residue at position 133 of said CL domain with a threonine residue and substitution of the serine residue at position 176 of said CL domain with a valine residue, wherein the sequence position numbers used herein for the CH1 and CL domains refer to Kabat numbering.

6. The protein construct of claim 5, which is a bispecific antibody.

7. The protein construct of claim 5, wherein the Fab CH1 domain of Ab1 is a mutated domain that derives from the CH1 domain of an immunoglobulin by substitution of the threonine residue at position 192 of said CH1 domain with an aspartic acid and the cognate CL domain is a mutated domain that derives from the CL domain of an immunoglobulin by substitution of the asparagine residue at position 137 of said CL domain with a lysine residue and substitution of the serine residue at position 114 of said CL domain with an alanine residue, and wherein the Fab CH1 domain of Ab2 is a mutated domain that derives from the CH1 domain of an immunoglobulin by substitution of the leucine residue at position 124 of said CH1 domain with a glutamine and substitution of the serine residue at position 188 of said CH1 domain with a valine residue, and the cognate CL domain is a mutated domain that derives from the CL domain of an immunoglobulin by substitution of the valine residue at position 133 of said CL domain with a threonine residue and substitution of the serine residue at position 176 of said CL domain with a valine residue, wherein the sequence position numbers used herein for the CH1 and CL domains refer to Kabat numbering.

8. The protein construct of claim 5, wherein the Fab CH1 domain of Ab2 is a mutated domain that derives from the CH1 domain of an immunoglobulin by substitution of the threonine residue at position 192 of said CH1 domain with an aspartic acid and the cognate CL domain is a mutated domain that derives from the CL domain of an immunoglobulin by substitution of the asparagine residue at position 137 of said CL domain with a lysine residue and substitution of the serine residue at position 114 of said CL domain with an alanine residue, and wherein the Fab CH1 domain of Ab1 is a mutated domain that derives from the CH1 domain of an immunoglobulin by substitution of the leucine residue at position 124 of said CH1 domain with a glutamine and substitution of the serine residue at position 188 of said CH1 domain with a valine residue, and the cognate CL domain is a mutated domain that derives from the CL domain of an immunoglobulin by substitution of the valine residue at position 133 of said CL domain with a threonine residue and substitution of the serine residue at position 176 of said CL domain with a valine residue.

9. The protein construct of claim 2, wherein the polypeptide linker sequence comprises an amino acid sequence selected from the group consisting of:

a) EPKX$_1$CDKX$_2$HX$_3$X$_4$PPX$_5$PAPELLGGPX$_6$X$_7$PPX$_8$PX$_9$PX$_{10}$GG (SEQ ID NO:1), wherein X$_1$, X$_2$, X$_3$, X$_4$, X$_5$, X$_6$, X$_7$, X$_8$, X$_9$, X$_{10}$, identical or different, are any amino acid;

b)
```
                                           (SEQ ID NO: 2)
EPKSCDKTHTSPPAPAPELLGGPGGPPGPGPGGG;
``` c)
```
                                           (SEQ ID NO: 3)
EPKSCDKTHTSPPAPAPELLGGPAAPPAPAPAGG;
``` d)
```
                                           (SEQ ID NO: 4)
EPKSCDKTHTSPPAPAPELLGGPAAPPGPAPGGG;
``` e)
```
                                           (SEQ ID NO: 5)
EPKSCDKTHTCPPCPAPELLGGPSTPPTPSPSGG;
or
``` f)
```
                                           (SEQ ID NO: 6)
EPKSCDKTHTSPPSPAPELLGGPSTPPTPSPSGG.
```

10. The protein construct of claim 1, wherein said protein construct specifically binds to both EGFR and HER2/neu.

11. The protein construct of claim 5, said protein construct being a multispecific antibody, wherein Ab1 and Ab2, being different, are independently selected from the group consisting of cetuximab or a mutated derivative thereof, and trastuzumab, or a mutated derivative thereof.

12. The protein construct of claim 1, wherein said protein construct specifically binds to both CD38 and PD-L1.

13. The protein construct of claim 5, said protein construct being a multispecific antibody wherein Ab1 and Ab2, being different, are independently selected from the group consisting of daratumumab or a mutated derivative thereof, and atezolizumab, or a mutated derivative thereof.

14. The protein construct of claim 12, said protein construct being a bispecific antibody that comprises: a) two heavy chains, each comprising SEQ ID NO:7 and b) four light chains, two comprising, SEQ ID NO:15, the two others comprising SEQ ID NO: 18.

* * * * *

UNITED STATES PATENT AND TRADEMARK OFFICE
CERTIFICATE OF CORRECTION

PATENT NO. : 11,560,437 B2
APPLICATION NO. : 16/498421
DATED : January 24, 2023
INVENTOR(S) : Eugene Zhukovsky, Olivier Leger and Richard J. Morse Page 1 of 1

It is certified that error appears in the above-identified patent and that said Letters Patent is hereby corrected as shown below:

In the Specification

Column 6,
Line 67, "via VH NL" should read --via VH /VL--.

Signed and Sealed this
Twenty-second Day of August, 2023

Katherine Kelly Vidal
*Director of the United States Patent and Trademark Office*